(12) United States Patent
Yamanaka et al.

(10) Patent No.: US 11,547,390 B2
(45) Date of Patent: Jan. 10, 2023

(54) ULTRASONIC CT APPARATUS AND ULTRASONIC IMAGING METHOD

(71) Applicant: Hitachi, Ltd., Tokyo (JP)

(72) Inventors: Kazuhiro Yamanaka, Tokyo (JP); Kenichi Kawabata, Tokyo (JP); Takahide Terada, Tokyo (JP); Yushi Tsubota, Tokyo (JP); Wenjing Wu, Tokyo (JP)

(73) Assignee: FUJIFILM HEALTHCARE CORPORATION, Chiba (JP)

( * ) Notice: Subject to any disclaimer, the term of this patent is extended or adjusted under 35 U.S.C. 154(b) by 419 days.

(21) Appl. No.: 15/762,574

(22) PCT Filed: Mar. 25, 2016

(86) PCT No.: PCT/JP2016/059535
§ 371 (c)(1),
(2) Date: Mar. 23, 2018

(87) PCT Pub. No.: WO2017/163389
PCT Pub. Date: Sep. 28, 2017

(65) Prior Publication Data
US 2018/0296194 A1    Oct. 18, 2018

(51) Int. Cl.
*A61B 8/08*    (2006.01)
*A61B 8/14*    (2006.01)
(Continued)

(52) U.S. Cl.
CPC ............ *A61B 8/5246* (2013.01); *A61B 8/08* (2013.01); *A61B 8/085* (2013.01); *A61B 8/145* (2013.01);
(Continued)

(58) Field of Classification Search
CPC ........... A61B 8/08; A61B 8/085; A61B 8/145; A61B 8/15; A61B 8/4416; A61B 8/4488;
(Continued)

(56) References Cited

U.S. PATENT DOCUMENTS

2003/0007598 A1* 1/2003 Wang .................. A61B 6/04
378/37
2003/0158481 A1 8/2003 Stotzka et al.
(Continued)

FOREIGN PATENT DOCUMENTS

JP    2004-520094 A    7/2004

OTHER PUBLICATIONS

Ernst Kretzek, et al., "Evaluation of directional reflectivity characteristics as new modality for 3D Ultrasound Computer Tomography," 2015 IEEE International Ultrasonics Symposium Proceedings.

(Continued)

*Primary Examiner* — Pascal M Bui Pho
*Assistant Examiner* — Alexei Bykhovski
(74) *Attorney, Agent, or Firm* — Mattingly & Malur, PC

(57) ABSTRACT

Information relevant to a state of a tissue in a subject (state information) is provided with technology reducing the amount of memory and computation necessary at the time of extracting the information. An ultrasonic wave is transmitted towards a subject, a transmission wave transmitted through the subject or a reflection wave reflected on the subject is received. A reception signal is generated on the basis of the transmission wave or the reflection wave. A tissue region candidate, of a region indicating a tissue of the subject, is set on the basis of the reception signal. State information, which is information relevant to a state of the tissue in the tissue region candidate, is calculated on the basis of the reception signal and the tissue region candidate. An ultrasonic image (Continued)

reflecting the state information is generated on the basis of the state information and displayed.

12 Claims, 25 Drawing Sheets

(51) Int. Cl.
    *A61B 8/15*     (2006.01)
    *A61B 8/00*     (2006.01)

(52) U.S. Cl.
    CPC .............. *A61B 8/15* (2013.01); *A61B 8/4416* (2013.01); *A61B 8/4488* (2013.01); *A61B 8/463* (2013.01); *A61B 8/469* (2013.01); *A61B 8/5207* (2013.01); *A61B 8/5223* (2013.01)

(58) Field of Classification Search
    CPC ....... A61B 8/463; A61B 8/469; A61B 8/5207; A61B 8/5223; A61B 8/5246
    See application file for complete search history.

(56) References Cited

U.S. PATENT DOCUMENTS

2008/0262354 A1* 10/2008 Yoshida ............... A61B 8/5238
                                                                       600/443
2018/0271492 A1* 9/2018 Jeon ........................ A61B 8/54

OTHER PUBLICATIONS

Nebojsa Duric, et al., "Detection of breast cancer with ultrasound tomography: First results with the Computed Ultrasound Risk Evaluation (CURE) prototype," Medical Physics 34, 773, 2007.
Matthias Birk, et al., "High-Speed Medical Imaging in 3D Ultrasound Computer Tomography," IEEE Trasactions on Parallel and Distributed Systems, Feb. 2016, vol. 27, No. 2, p. 455-467.
Ernst Kretzek, Evaluation of directional reflectivity characteristics as new modality for 3D Ultrasound Computer Tomography, 2015 IEEE International Ultrasonics Symposium Proceeding.
International Search Report of PCT/JP2016/059535 dated May 24, 2016.

* cited by examiner

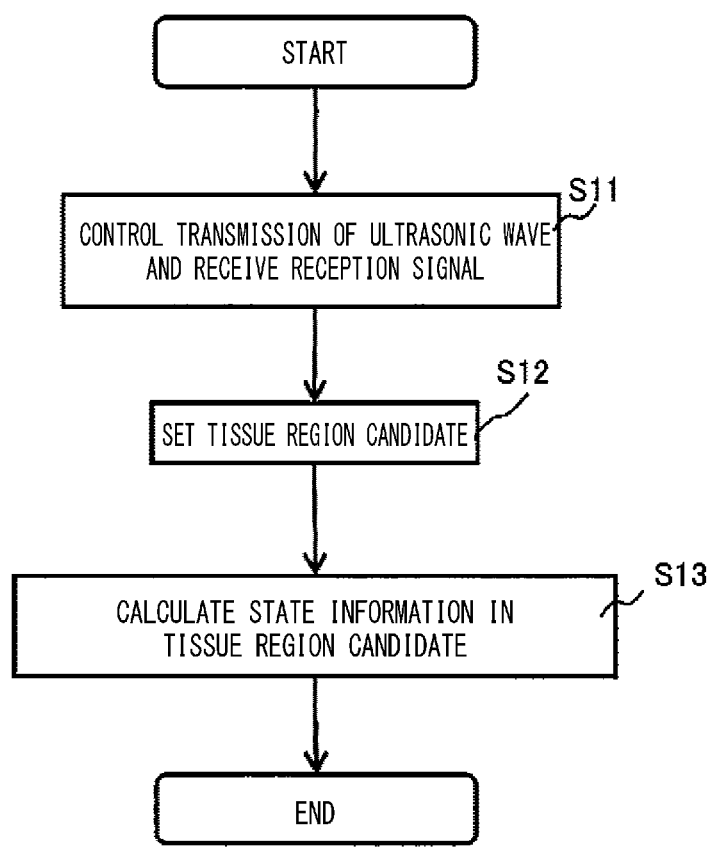

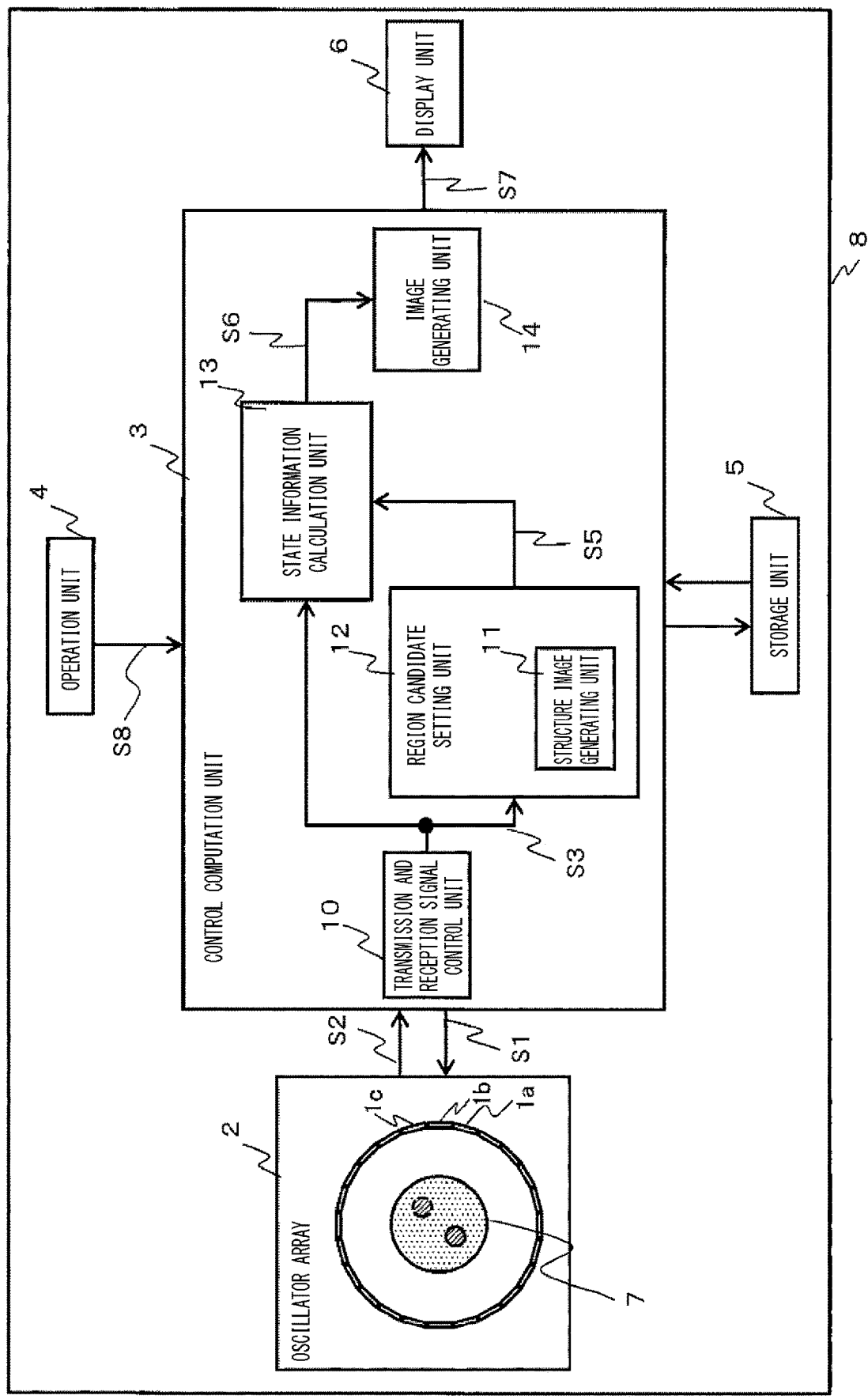

FIG. 4A

| NUMBER OF TIMES OF TRANSMISSION (N) | OSCILLATOR | SWITCH | APODIZATION | DELAY TIME |
|---|---|---|---|---|
| 1 | OSCILLATOR 1a | ON | 1 | 1.0 μs |
| 1 | OSCILLATOR 1b | ON | 1 | 0.0 μs |
| 1 | OSCILLATOR 1c | ON | 1 | 1.0 μs |
| 1 | OSCILLATOR 1d | OFF | – | – |
| ⋮ | ⋮ | ⋮ | ⋮ | ⋮ |
| 1 | OSCILLATOR 1x | OFF | – | – |
| 2 | OSCILLATOR 1a | OFF | – | – |
| 2 | OSCILLATOR 1b | OFF | – | – |
| 2 | OSCILLATOR 1c | OFF | – | – |
| 2 | OSCILLATOR 1d | ON | 1 | 1.0 μs |
| 2 | OSCILLATOR 1e | ON | 1 | 0.0 μs |
| 2 | OSCILLATOR 1f | ON | 1 | 1.0 μs |
| 2 | OSCILLATOR 1g | OFF | – | – |
| ⋮ | ⋮ | ⋮ | ⋮ | ⋮ |
| 2 | OSCILLATOR 1x | OFF | – | – |
| 3 | OSCILLATOR 1a | OFF | – | – |
| ⋮ | ⋮ | ⋮ | ⋮ | ⋮ |

FIG.4B

| NUMBER OF TIMES OF TRANSMISSION (N) | OSCILLATOR | SWITCH | APODIZATION |
|---|---|---|---|
| 1 | OSCILLATOR 1a | ON | 1 |
| 1 | OSCILLATOR 1b | ON | 1 |
| 1 | OSCILLATOR 1c | ON | 1 |
| 1 | OSCILLATOR 1d | ON | 1 |
| ⋮ | ⋮ | ⋮ | ⋮ |
| 1 | OSCILLATOR 1x | ON | 1 |
| 2 | OSCILLATOR 1a | ON | 1 |
| 2 | OSCILLATOR 1b | ON | 1 |
| ⋮ | ⋮ | ⋮ | ⋮ |
| 2 | OSCILLATOR 1x | ON | 1 |
| 3 | OSCILLATOR 1a | ON | 1 |
| 3 | OSCILLATOR 1b | ON | 1 |
| ⋮ | ⋮ | ⋮ | ⋮ |

120 121 122 123 124

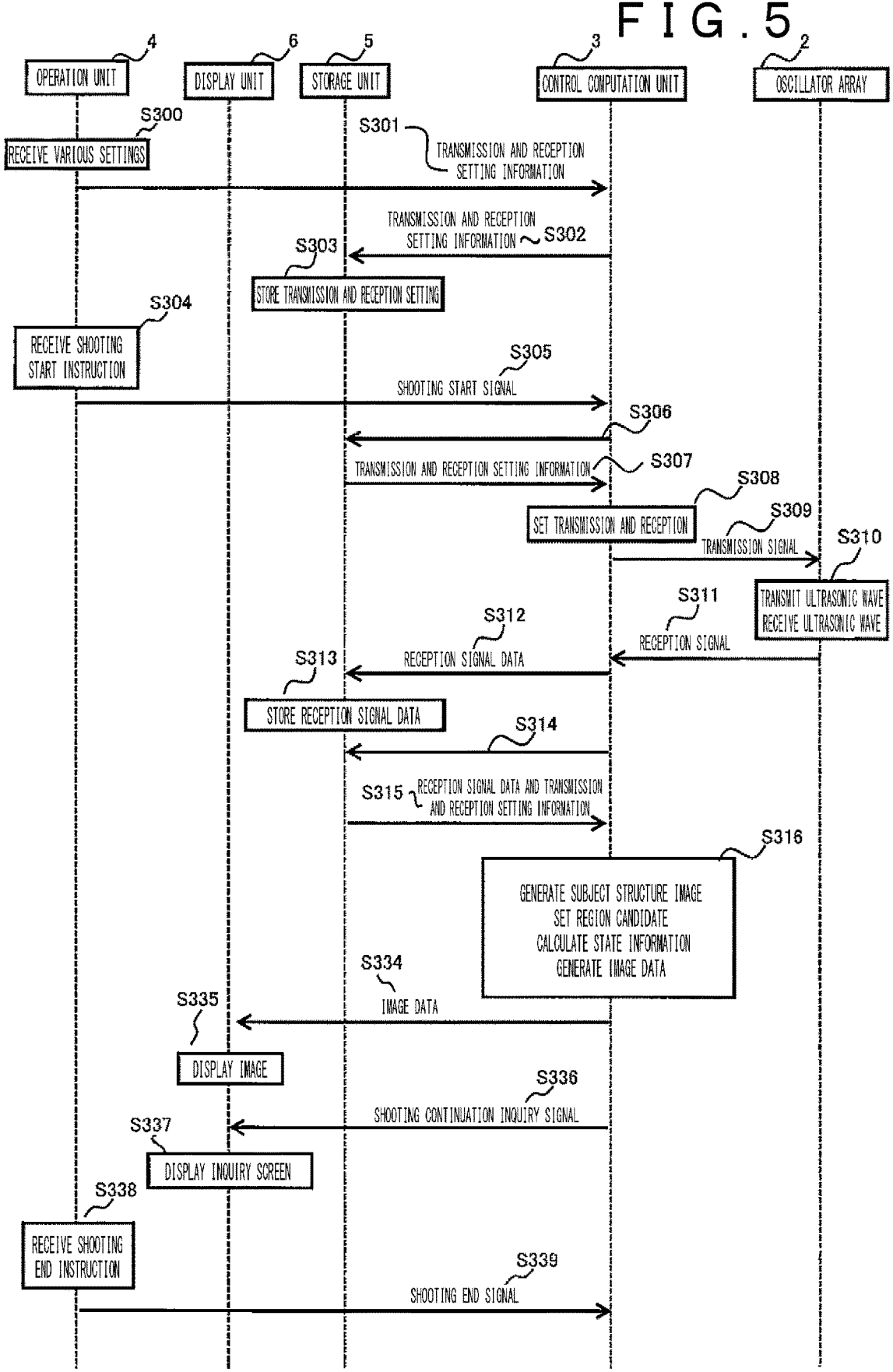

61 RECEPTION SIGNAL INTENSITY PATTERN OF REFLECTION POINT B

62 RECEPTION SIGNAL INTENSITY PATTERN OF REFLECTION POINT A

| NUMBER OF TIMES OF TRANSMISSION AND RECEPTION (S81) | TRANSMISSION OSCILLATOR (70) | RECEPTION OSCILLATOR (50, 55) |
|---|---|---|
| 1 | 1a~1c | 1a~1c |
| 2 | 1d~1f | 1a~1c |
| ⋮ | ⋮ | ⋮ |

| NUMBER OF TIMES OF TRANSMISSION AND RECEPTION (S81) | TRANSMISSION OSCILLATOR (70) | RECEPTION OSCILLATOR (50, 55) |
|---|---|---|
| 1 | 1a~1c | 1a~1c |
| 2 | 1a~1c | 1d~1f |
| ⋮ | ⋮ | ⋮ |

| NUMBER OF TIMES OF TRANSMISSION AND RECEPTION | TRANSMISSION OSCILLATOR | RECEPTION OSCILLATOR |
|---|---|---|
| 1 | 1a~1c | 1a~1c |
| 2 | 1a~1c | 1d~1f |
| 3 | 1a~1c | 1g~1i |
| ⋮ | ⋮ | ⋮ |
| 8 | 1a~1c | 1v~1x |
| 9 | 1d~1f | 1a~1c |
| 10 | 1d~1f | 1d~1f |
| 11 | 1d~1f | 1g~1i |
| 12 | 1d~1f | 1j~1l |
| ⋮ | ⋮ | ⋮ |

ULTRASONIC CT APPARATUS AND ULTRASONIC IMAGING METHOD

TECHNICAL FIELD

The present invention relates to an ultrasonic CT apparatus and an ultrasonic imaging method.

BACKGROUND ART

There is a technology described in "Evaluation of directional reflectivity characteristics as new modality for 3D Ultrasound Computer Tomography" (Non-Patent Document 1), as an ultrasonic imaging apparatus in which an ultrasonic wave is transmitted with respect to a subject such as a biological body from an oscillator, the ultrasonic wave reflected on the subject, or the ultrasonic wave transmitted through the subject is received, and information relevant to the subject is measured. In Non-Patent Document 1, a method is described in which reflection properties are calculated by utilizing that the reflection properties at each reflection point on a boundary of the subject or in the subject depend on a texture of a structure and a boundary surface of the subject, in an ultrasonic imaging apparatus (an ultrasonic computed tomography (CT) apparatus) in which oscillators are three-dimensionally arranged. In addition, a possibility of distinguishing the state of the boundary of the subject and the interior tissue from the reflection properties is mentioned.

CITATION LIST

Non-Patent Document

Non-Patent Document 1: Ernst Kretzek, Patrick Hucker, Michael Zapf and Nicole V. Ruiter; "Evaluation of directional reflectivity characteristics as new modality for 3D Ultrasound Computer Tomography," in Ultrasonics Symposium (IUS), 2015 IEEE International, 0182, (2015)

Non-Patent Document 2: N. Duric, P. Littrup, L. Poulo, A. Babkin, R. Pevzner, E. Holsapple, et al., "Detection of breast cancer with ultrasound tomography: first results with the Computed Ultrasound Risk Evaluation (CURE) prototype," Med. Phys., 34, pp. 773-85 (February, 2007).

SUMMARY OF THE INVENTION

Problems to be Solved by the Invention

In the method of Non-Patent Document 1, in the ultrasonic imaging apparatus in which the oscillators are three-dimensionally arranged, the reflection properties at all points in a shooting (imaging) space region, which is a region transmitting and receiving the ultrasonic wave, are calculated, computation based on a vast amount of memory of 1.4 terabyte (TB) per one shooting at a maximum is requested, and calculation for a long period of time (for a few hours) is required. For this reason, the method of Non-Patent Document 1, for example, is not suitable for an ultrasonic imaging apparatus of a medical application or the like using a biological body as a target (for example, breast cancer examination) in which it is required that a result is displayed for a short period of time (for 10 minutes to 15 minutes).

An object of the present invention is to provide a technology for reducing an amount of memory and an amount of computation, which are necessary at the time of extracting information relevant to a state of a tissue in a subject.

Solutions to Problems

According to the present invention, in order to attain the object described above, an ultrasonic CT apparatus as described below is provided. That is, the ultrasonic CT apparatus is an ultrasonic CT apparatus, including: an oscillator array which transmits an ultrasonic wave towards a subject, receives a transmission wave transmitted through the subject or a reflection wave reflected on the subject, and transmits a reception signal based on the transmission wave or the reflection wave; a signal receiving unit which receives the reception signal; a region candidate setting unit which sets a candidate of a region indicating a tissue of the subject (a tissue region candidate), on the basis of the reception signal; a state information calculation unit which calculates state information of the tissue in the tissue region candidate, on the basis of the reception signal and the tissue region candidate; an image generating unit which generates an ultrasonic image reflecting the state information, on the basis of the state information; and a display unit which displays the ultrasonic image.

Effects of the Invention

According to the present invention, is possible to reduce an amount of memory and an amount of computation, which are necessary at the time of extracting information relevant to a state of a tissue in a subject.

Other objects, configurations, and effects will be obvious according to the following embodiments.

BRIEF DESCRIPTION OF THE DRAWINGS

FIG. 1 is an example of a flowchart illustrating an outline of an operation of a control computation unit of an ultrasonic imaging apparatus.

FIG. 2 is an example of a block diagram illustrating a configuration of an ultrasonic imaging apparatus of a first embodiment.

FIG. 4A is an example of a transmission setting table.

FIG. 4B is an example of a reception setting table.

FIG. 5 is an example of a sequence diagram illustrating the operation of the ultrasonic imaging apparatus.

MODE FOR CARRYING OUT THE INVENTION

Figure 3A:
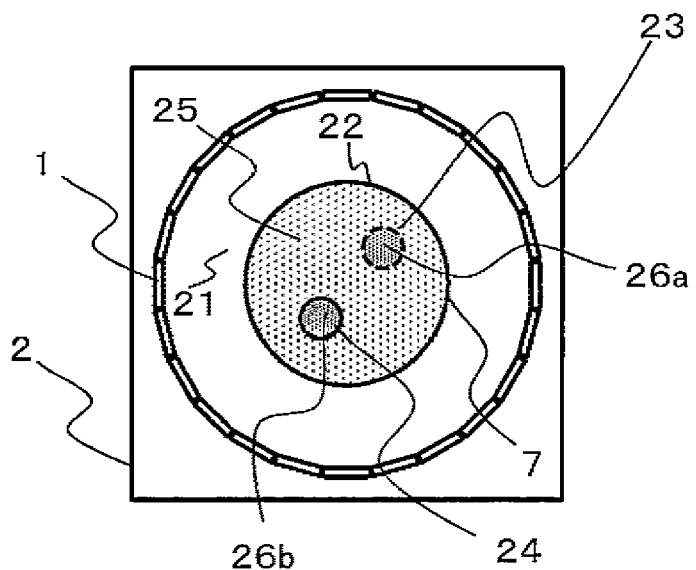
FIG. 3A is a diagram illustrating an example of a subject, which is a shooting target.

Hereinafter, examples will be described by using the drawings.

<Outline>

First, the outline will be described.

An ultrasonic imaging apparatus (an ultrasonic transmission and reception apparatus) includes an oscillator array transmitting and receiving an ultrasonic wave with respect to a subject, and a control computation unit calculating state information, which is information relevant to a state (properties and (or) a state) an interior of the subject by controlling the oscillator array.

FIG. 1 is an example of a flowchart illustrating an outline of an operation of the control computation unit of the ultrasonic imaging apparatus.

The control computation unit controls the transmission of the ultrasonic wave with respect to the oscillator array, and receives a signal (a reception signal) based on the ultrasonic wave received from the subject, from the oscillator array (S11). Specifically, a transmission and reception signal control unit of the control computation unit transmits a signal (an instruction) transmitting the ultrasonic wave with respect to the subject, with respect to the oscillator array, and receives the reception signal from the oscillator array (S11).

Next, the control computation unit sets a tissue region candidate, which is a candidate of a region indicating a tissue of the subject (S12). Specifically, a region candidate setting unit of the control computation unit sets the tissue region candidate on the basis of the reception signal received from the oscillator array (S12). Next, the control computation unit calculates state information in the tissue region candidate (S13). Specifically, a state information calculation unit of the control computation unit calculates the state information on the basis of the reception signal received in Step S11 and the tissue region candidate set in Step S12 (S13).

As described above, the ultrasonic imaging apparatus calculates the state information in the tissue region candidate in the subject, that is, calculates state information on the basis of the reception signal of a part corresponding to the tissue region candidate in the reception signals from the subject, and thus, it is possible to reduce an amount of memory and an amount of computation, which are necessary at the time of calculating the state information, compared to the case of calculating the state information from all of the reception signals from the subject.

First Embodiment

Next, a first embodiment, which is a detailed embodiment of the present invention, will be described.

FIG. 2 is an example of a block diagram illustrating the entire configuration of an ultrasonic imaging apparatus 8. An example will be described in which breasts are examined by using the ultrasonic imaging apparatus 8.

The ultrasonic imaging apparatus 8 includes an oscillator array 2 including a plurality of oscillators $1a$ to $1c$ which transmit (send) an ultrasonic wave with respect to a subject 7, a control computation unit 3 connected to at least two or more oscillators in the plurality of oscillators $1a$ to $1c$, an operation unit (an interface (IF)) 4 connected to the control computation unit 3, a storage unit 5, and a display unit 6.

The oscillator array 2, for example, is provided in a tank filled with an acoustic impedance matching material, which is a liquid through which an ultrasonic wave is easily transmitted. The acoustic impedance matching material is a liquid (an acoustic impedance matching liquid) for matching an acoustic impedance of a propagation path of an ultrasonic wave, and for example, is degassed water, gel, or the like.

The plurality of oscillators 1a to 1c or the like are controlled by the computation unit 3 to oscillate, transmit (send) an ultrasonic wave towards the subject 7 in the oscillator array 2 as an ultrasonic signal, and receive an ultrasonic wave having an interaction with the subject 7 (a reflection wave (an ultrasonic wave reflected on the subject 7) and a transmission wave (an ultrasonic wave propagated (transmitted) through the subject 7 without being reflected on the subject 7)) and (or) an ultrasonic wave not having an interaction with the subject 7 (an ultrasonic wave not transmitted through the subject 7), as the ultrasonic signal. That is, the plurality of oscillators 1a to 1c or the like are ultrasonic transducers which converts an electric signal received from the control computation unit 3 into an ultrasonic signal to be transmitted into the oscillator array 2, and converts the ultrasonic signal reflecting a state in the subject 7, which is received from the oscillator array 2, into an electric signal to be transmitted into the control computation unit 3.

The control computation unit 3 controls an operation of each functional unit in the ultrasonic imaging apparatus 8. In addition, the control computation unit 3 transmits the electric signal into at least two oscillators 1 in the plurality of oscillators 1a to 1c or the like, analyzes the electric signal received from the oscillator 1, performs predetermined computation, and calculates state information in the subject 7.

In addition, the control computation unit 3 includes a transmission and reception signal control unit 10, a region candidate setting unit 12, a state information calculation unit 13, and an image generating unit 14.

The control computation unit 3, for example, may be configured of hardware by being designed as an integrated circuit such as a field-programmable gate array (FPGA) or an application specific integrated circuit (ASIC). In addition, the control computation unit 3 is a processor, and executes a program (not illustrated) stored in advance in a memory (not illustrated), and thus, the function of each of the functional units 10 to 14 may be configured. In this case, in the following description, processing executed by the control computation unit 3 is actually executed by a processor corresponding to the control computation unit 3.

The transmission and reception signal control unit 10 transmits a transmission signal S1, which is an electric signal transmitting an ultrasonic wave, to the oscillator array 2, on the basis of transmission and reception setting information S8, which includes various setting information items at the time of transmitting and receiving the ultrasonic wave and is one type of input received from the operation unit 4, and receives a reception signal S2, which is generated by converting the ultrasonic wave into an analog electric signal by the oscillator array 2, from the oscillator array 2. That is, the transmission and reception signal control unit 10 is a signal receiving unit and a signal transmitting unit. In addition, the transmission and reception signal control unit inputs the entire reception signal S2 or a part of the reception signal S2 into an analog-to-digital (A/D) converter, generates a reception signal data S3, which is a digital electric signal, and transmits the reception signal data S3 to the region candidate setting unit 12 and the state information calculation unit 13.

The region candidate setting unit 12 includes a structure image generating unit 11 generating a subject structure image S4, which is an image indicating a structure of the subject 7, on the basis of the reception signal data S3 generated by the transmission and reception signal control unit 10. The region candidate setting unit 12 sets a tissue region candidate S5 on the basis of the subject structure image S4 or the reception signal data S3, and transmits the tissue region candidate S5 to state information calculation unit 13.

The state information calculation unit 13 calculates state information S6 in the tissue region candidate S5 on the basis of the reception signal data S3 and the region candidate S5, and transmits the state information S6 to the image generating unit 14.

The image generating unit 14 generates an image relevant to the subject 7 on the basis of the state information S6. Specifically, the image generating unit 14 generates image data S7 of an image relevant to state information displaying the state information (an image reflecting the state information) in the shape easy to be understood by an operator. Furthermore, generating the image data may be expressed as generating an image. Then, the image generating unit 14 transmits the generated image data S7 to the storage unit 5.

The operation unit 4 receives input of various information items controlling the ultrasonic imaging apparatus 8 from the operator (for example, information or the like relevant to the transmission and reception setting information S8 and various instructions), transmits the received input to the control computation unit 3, and applies an instruction to the control computation unit 3, according to an operation performed by the operator with respect to the operation unit 4. In addition, the operation unit 4 may perform communication of information with respect to other devices.

The storage unit 5 stores various information items received by the ultrasonic imaging apparatus 8 and (or) subject information, which is information relevant to the subject 7 from the control computation unit 3. Specifically, the storage unit 5 stores (retains) the transmission and reception setting information S8 of an information storage table group 100 illustrated in FIG. 4, the reception signal data S3, the image information items S4 to S7, and the like. In addition, the storage unit 5 performs communication of information to be stored along with the control computation unit 3, according to the instruction from the control computation unit 3.

The display unit 6 displays the image generated by the image generating unit 14. Specifically, the display unit 6 receives the image data S7 from the storage unit 5 through the control computation unit 3, and displays the image data S7, which is a measurement result of the subject 7. In addition, the display unit 6 may display a procedure of the operation of the ultrasonic imaging apparatus 8 and (or) an option of the instruction applied by the operator.

Each of the functional units 10 to 14 configuring the control computation unit 3 is connected to the operation unit and the storage unit 5, and the operator inputs various information items to the operation unit 4, and thus, the operation of each of the functional units 10 to 14 is changed, or the storage unit 5 communicates with various information items, the subject information, and the like.

Here, the subject structure image is an image generated on the basis of the transmitted and received ultrasonic signal, for example, a B mode image according to an ultrasonic echo method (an image based on a reflection wave)) and an image using a physical property value according to an ultrasonic tomography method (an acoustic velocity and attenuation) (an image based on a transmission wave).

In addition, the tissue region candidate (hereinafter, referred to as a "region candidate") includes a boundary region candidate, which is a candidate of a region indicating a boundary of the tissue in the subject 7, and an interior region candidate, which is a candidate of a region indicating an interior of the tissue in the subject 7. In the region candidate setting unit 12, at least one of the boundary region candidate and the interior region candidate is set as the region candidate.

In addition, the state information includes boundary state information, which is the state information of the boundary of the tissue in the subject 7, and interior state information, which is the state information of the interior of the tissue in the subject 7. In the state information calculation unit 13, at least one of the boundary state information and the interior state information is calculated as the state information.

In addition, the state information includes state information based on a reflection wave and state information based on a transmission wave. The state information based on the reflection wave is state information reflecting reflection properties of each reflection point in the subject 7, which is generated on the basis of the ultrasonic signal (the reflection signal) reflected on the subject 7. Here, the reflection properties are properties of the reflection point, which are calculated on the basis of a change in the reflection signal at the time of changing at least one of an oscillator transmitting an ultrasonic wave (a transmission oscillator) and an oscillator receiving an ultrasonic wave (a reception oscillator), with respect to a reflection signal from one reflection point.

The boundary state information based on the reflection wave, for example, includes surface roughness of a boundary surface of the tissue, which is calculated on the basis of directionality of the reflection signal, a difference in acoustic impedance between the tissues, and the like.

The interior state information based on the reflection wave, for example, includes a density of a fine scattering body causing the ultrasonic wave to scatter in the tissue, a typical size of the fine scattering body, a difference in acoustic impedance between the entire tissue and the fine scattering body, and the like.

The state information based on the transmission wave is state information reflecting a physical property value of each transmission point in the subject 7, which is generated on the basis of the ultrasonic signal (the transmission signal) transmitted through the subject 7.

The boundary state information based on the transmission wave, for example, includes attenuation of a transmission signal intensity reflecting the acoustic impedance between the tissues, and the like.

The interior state information based on the transmission wave, for example, includes attenuation of the transmission signal intensity reflecting absorption and (or) scattering of the ultrasonic wave in the tissue in the subject 7, a propagation velocity (an acoustic velocity) of the ultrasonic wave depending on properties of the tissue, and the like.

Furthermore, the subject information includes the reception signal data S3, the image information (the subject structure image S4, the subject boundary information, which is information relevant to the boundary of the tissue of the subject 7 (the boundary region candidate S5 and the boundary state information S6), the subject interior information, which is information relevant to the interior of the tissue in the subject 7 (the boundary state information S5 and the interior state information S6), and the image data S7) (hereinafter, referred to as the "image information items S4 to S7"), and the like.

As described above, the ultrasonic imaging apparatus 8 is an ultrasonic computed tomography (CT) apparatus, which transmits the ultrasonic wave to the subject 7, and configures again the ultrasonic image, which is a tomographic image of the subject 7, by using the reflection wave and (or) the transmission wave received from the subject 7.

Next, the outline of image information items S4 to S7 according to each of the functional units 10 to 14 of the control computation unit 3 in a case where the ultrasonic imaging apparatus 8 calculates the subject boundary information, will be described by using FIG. 3.

FIG. 3A is a diagram illustrating an example of the subject 7, which is a shooting target. The subject 7 is breasts, and is disposed in a region 21 in the oscillator array 2, which is filled with an acoustic matching material such as degassed water or the like, an outer circumference of the subject 7 is covered with a skin 22, and a great majority of the interior of the skin 22 is filled with a fatty tissue 25. Two tissues (for example, growths) 26a and 26b further exist in the fatty tissue 25. A boundary 23 between the growth 26a and the skin 22 is a boundary surface having large roughness. A state of the boundary surface having large roughness will be referred to as "rough". On the other hand, a boundary 24 between the growth 26b and the skin 22 is a boundary surface having small roughness. A state of the boundary surface having small roughness will be referred to as "smooth".

Figure 3B:
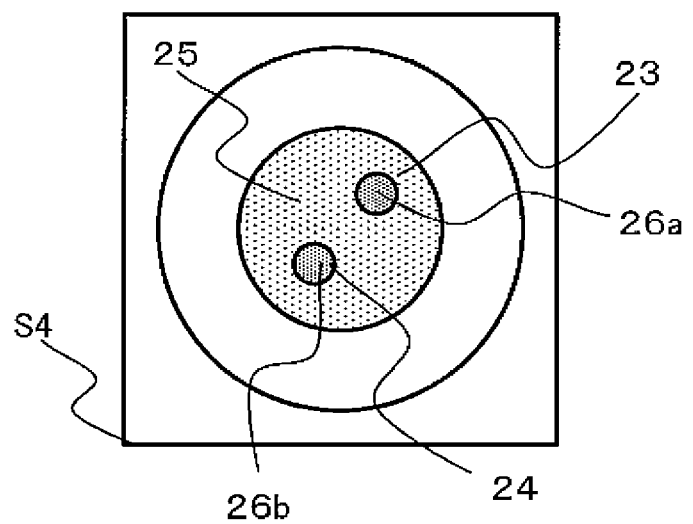
FIG. 3B is a diagram illustrating an example of a subject structure image generated by a structure image generating unit.

FIG. 3B is a diagram illustrating an example of the subject structure image S4 generated by the structure image generating unit 11. In the subject structure image S4 illustrated in FIG. 3B, the fatty tissue 25 and the growth 26 are distinguished from each other as the subject structure, but a difference between the boundary 23 and the boundary 24 is not capable of being discriminated.

Figure 3C:
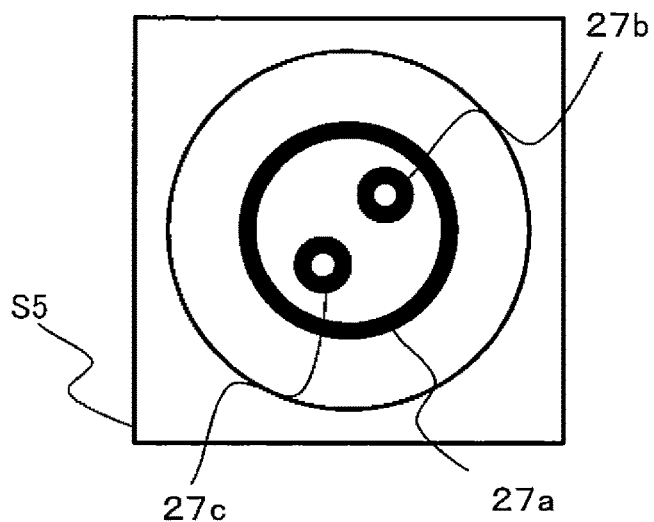
FIG. 3C is a diagram illustrating an example of a boundary region candidate set by a region candidate setting unit.

FIG. 3C is a diagram illustrating an example of the boundary region candidate S5 set by the region candidate setting unit 12. In FIG. 3C, portions 27a to 27c in which a brightness value of the subject structure image S4 is greatly different from the circumference (exceeds a predetermined threshold value), are set as the boundary region candidate S5.

Furthermore, as illustrated in FIG. 3C, the boundary region candidate S5 does not include information other than the boundary region candidate S5 (for example, information of the interior of the skin 22, such as the fatty tissue 25, and the growths 26a and 26b).

Figure 3D:
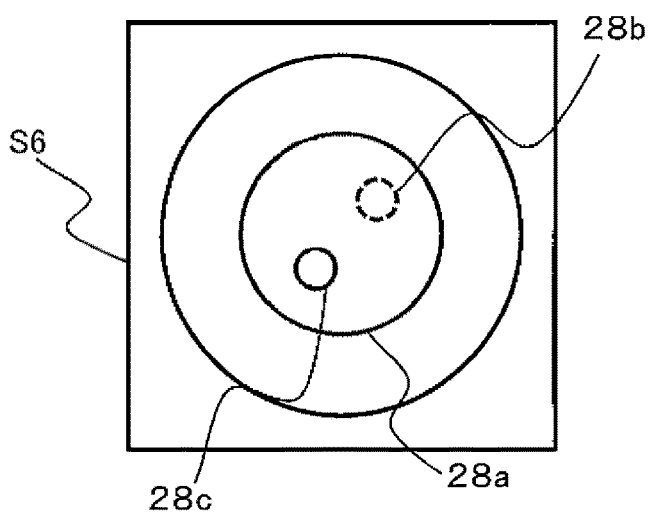
FIG. 3D is a diagram illustrating an example of boundary state information generated by a state information calculation unit.

FIG. 3D is a diagram illustrating an example of the boundary state information S6 calculated by the state information calculation unit 13. In FIG. 3D, the boundary state information S6 in the portions 27a to 27c, which is the boundary region candidate S5, is calculated. In addition, it is illustrated that portions 28a and 28c, which are the boundary state information S6, are a smooth boundary, and a portion 28b is a rough boundary.

Figure 3E:
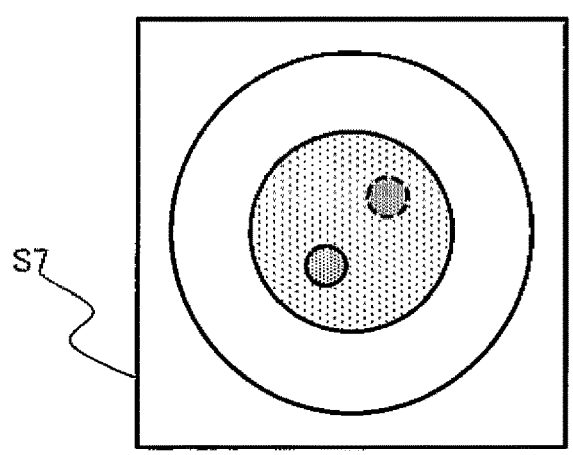
FIG. 3E is a diagram illustrating an example of image data generated by an image generating unit.

FIG. 3E is a diagram illustrating an example of the image data S7 generated by the image generating unit 14. In FIG. 3E, the subject structure image S4 is laid out in a gray scale, and image data in which the boundary state information S6 is laid out in a color map to be overlaid on the subject structure image S4, is generated only in a region of the boundary region candidate S5 (that is, the portions 27a to 27c). In addition, for example, the image data S7 may be generated in which the boundary state information S6 is laid out in the gray scale.

Figure 3F:
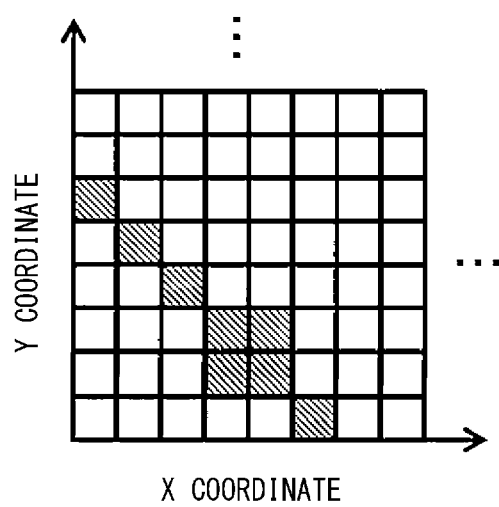
FIG. 3F is a diagram illustrating an example of an image configuration of each of image information items S4 to S7.

FIG. 3F is a diagram illustrating an example of an image configuration of each of the image information items S4 to S7. In FIG. 3F, it is illustrated that each of the image information items S4 to S7 is retained as pixel data partitioned into the shape of a grid. In addition, each of the image information items S4 to S7, for example, may be retained as three-dimensional voxel data. In addition, a partitioning method of a pixel or a voxel may be a method of partitioning the pixel or the voxel into the shape of a grid of an orthogonal coordinate system as illustrated in FIG. 3F, or may be a method of partitioning the pixel or the voxel into an arbitrary shape by using a polar coordinate system. A partition shape and the size of the pixel or the voxel may be adaptively set according to a transmission and reception method of an ultrasonic wave and (or) the structure of the subject.

FIG. 4 is a diagram illustrating an example of the information storage table group 100 stored in the storage unit 5. The information storage table group 100 of FIG. 4 illustrates an example in which a predetermined number of oscillators 1 transmit the ultrasonic wave at the time of transmitting the ultrasonic wave, all of the oscillators 1 receive the ultrasonic wave at the time of receiving the ultrasonic wave, and the oscillator 1 transmitting the ultrasonic wave is changed for each time of transmission and reception, in the transmission and reception of the ultrasonic wave of one time.

FIG. 4A is an example of a transmission setting table 110 including transmission setting information S8a, which is setting information at the time of transmitting the ultrasonic wave, in the transmission and reception setting information S8 of the ultrasonic wave. Furthermore, the storage unit 5 may include the transmission setting table 110 for each time of transmitting the ultrasonic wave (each time of transmission), as the transmission setting table group.

The transmission setting table 110 includes the number of times of transmission 111, an oscillator 112, which is a control target, a switch 113 indicating ON/OFF of the oscillator 1, apodization 114 of the oscillator 1, and delay time 115, which is a timing of transmitting the ultrasonic wave to be applied to the oscillator 1. In addition, the transmission setting information S8a also includes a setting value, which is a constant value (a common value) with respect to the entire number of times of transmission (not illustrated), such as a time interval between the respective times of transmission, and a gain and a filter constant of an amplifier at the time of transmitting the ultrasonic wave.

FIG. 4B is an example of a reception setting table 120 including reception setting information S8b, which is setting information at the time of receiving the ultrasonic wave, in the transmission and reception setting information S8 of the ultrasonic wave. Furthermore, the storage unit 5 may include the reception setting table 120 for each time of receiving the (each time of reception), as the reception setting table group.

The reception setting table 120 includes the number of times of reception 121, an oscillator 122, which is a control target, a switch 123 indicating ON/OFF of the oscillator 1, and apodization 124 of the oscillator 1. In addition, the reception setting information S8b also includes a setting value, which is a constant value (a common value) with respect to the entire number of times of reception (not illustrated), such as a time interval between the respective receptions, and a gain and a filter constant of an amplifier at the time of receiving the ultrasonic wave.

Next, the ultrasonic imaging apparatus 8, in particular, the operation of the control computation unit 3 will be described in detail by using FIG. 5 to FIG. 11.

FIG. 5 is an example of a sequence diagram illustrating the operation of the ultrasonic imaging apparatus 8.

In a case where various setting information items from the operator are received (S300), the operation unit 4 transmits the transmission and reception setting information S8 to the control computation unit 3 (S301). The control computation unit 3 transmits the received transmission and reception setting information S8 to the storage unit 5 (S302), and the storage unit 5 stores the transmission and reception setting information S8 (S303).

Then, in a case where a shooting start instruction from the operator is received (S304), the operation unit 4 transmits a shooting start signal S20 indicating the shooting start instruction to the control computation unit 3 (S305). The control computation unit 3 receiving the shooting start signal S20 starts a transmission and reception setting operation, and in a case where the transmission and reception setting operation is completed, a measurement operation is started.

In the transmission and reception setting operation, the control computation unit 3 acquires the transmission and reception setting information S8 with respect to the storage unit 5 (S306), and receives the transmission and reception setting information S8 from the storage unit 5 (S307). The control computation unit 3 performs transmission and reception setting, which is setting relevant to the oscillator 1 transmitting and receiving the ultrasonic wave, according to the received transmission and reception setting information S8 (S308).

Next, in the measurement operation, the control computation unit 3 transmits the transmission signal S1 to the oscillator array 2, according to the transmission and reception setting information S8 set in Step S308 (S309). The oscillator array 2 receiving the transmission signal S1 transmits the ultrasonic wave into the oscillator array 2, and receives the ultrasonic wave from the oscillator array 2 (S310). The oscillator array 2 converts the received ultrasonic wave into the reception signal S2, and transmits the reception signal S2 to the control computation unit 3 (S311).

The control computation unit 3 transmits the reception signal data S3 based on the received reception signal S2 to the storage unit 5 (S312), and the storage unit 5 stores the reception signal data S3 (S313). The control computation unit 3 repeats Step S309 to Step S313 according to the transmission and reception setting set in Step S308, and stores a plurality of reception signal data items S3 (for each time of transmission and reception) in the storage unit 5.

Then, the control computation unit 3 acquires the reception signal data S3 and the transmission and reception setting information S8 for each time of transmission and reception with respect to the storage unit 5 (S314), and receives the reception signal data S3 and the transmission and reception setting information S8 from the storage unit 5 (S315). The control computation unit 3 generates the subject structure image S4 on the basis of the received reception signal data S3 and the transmission and reception setting information S8 for each time of transmission and reception, sets the region candidate S5 on the basis of the subject structure image S4, calculates the state information S6 on the basis of the reception signal data S3, the region candidate S5, and the transmission and reception setting information S8 for each time of transmission and reception, and generates the image data S7 on the basis of the subject structure image S4 and the state information S6 (S316). Then, the control computation unit 3 transmits the image data S7 to the display unit 6 (S334). The display unit 6 displays an image based on the received image data S7 (S335).

Next, the control computation unit 3 transmits a shooting continuation inquiry signal S21 inquiring whether or not to continue the shooting, to the display unit 6 (S336). The display unit 6 displays an inquiry screen inquiring whether or not to continue the measurement of the operator, on the basis of the received shooting continuation inquiry signal S21 (S337). In a case where a shooting end instruction is received from the operator (S338), the operation unit 4 transmits a shooting end signal S22 indicating the shooting end instruction, to the control computation unit 3 (S339).

The control computation unit 3 receiving the shooting end signal S22 ends the processing.

Figure 6:
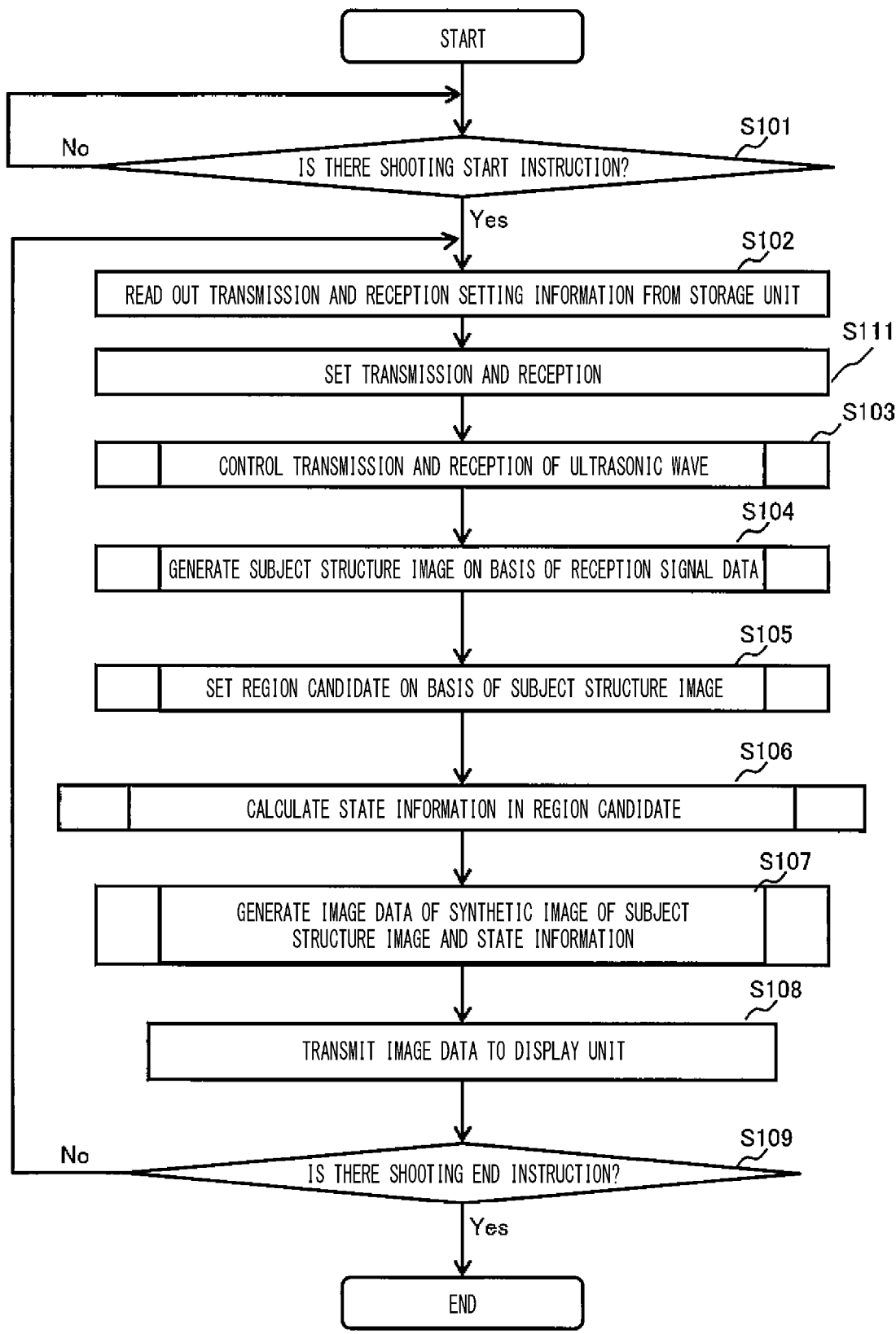
FIG. 6 is an example of a flowchart illustrating a flow of the entire operation of the control computation unit.

FIG. 6 is an example of a flowchart illustrating the entire flow of the operation of the control computation unit 3.

The control computation unit 3 receives the shooting start signal S20 from the operation unit 4, and thus, determines the presence or absence of the shooting start instruction (S101). Furthermore, the control computation unit 3 may determine that there is the shooting start instruction according to a power activation of the ultrasonic imaging apparatus 8. In a case where there is no shooting start instruction (No in S101), the control computation unit 3 determines again the presence or absence of the shooting start instruction. In a case where there is the shooting start instruction (Yes in S101), the control computation unit 3 starts the transmission and reception setting operation (S102 and S111). The transmission and reception signal control unit 10 reads out the transmission and reception setting information S8 stored in the information storage table group 100 from the storage unit (S102), stores the read transmission and reception setting information S8 in the transmission and reception signal control unit 10, and performs the transmission and reception setting such as setting of the number of times of transmission and reception of the ultrasonic wave (the number of times of transmission and reception), and setting of the oscillator 1 to be used for each time of transmission and reception (S111).

Then, the control computation unit 3 starts the measurement operation (S103 to S108). The transmission and reception signal control unit 10 controls the oscillator array 2 such that the ultrasonic wave according to the transmission and reception setting information S8 set in Step S111 is transmitted and received (S103). The details of Step S103 will be described below in FIG. 7. The structure image generating unit 11 generates the subject structure image S4, on the basis of the reception signal data S3 generated in Step S103 and the transmission and reception setting information S8 set in Step S111 (S104). The details of Step S104 will be described below in FIG. 8.

The region candidate setting unit 12 sets the region candidate S5 on the basis of the subject structure image S4 generated in Step S104 (S105). The details of Step S105 will be described below in FIG. 9. The state information calculation unit 13 calculates the state information S6 in the region candidate S5 set in Step S105 (S106). The details of Step S106 will be described below in FIG. 10. The image generating unit 14 generates the image data S7, which is data of a synthetic image of the subject structure image S4 generated in Step S104 and the state information S6 calculated in Step S106 (S107).

Then, the image generating unit 14 transmits the image data S7 to the display unit 6, and displays the synthetic image based on the image data S7 on the display unit 6 (S108).

Next, the control computation unit 3 determines the presence or absence of the shooting end instruction (S109). Specifically, the control computation unit 3 transmits the shooting continuation inquiry signal S21 to the display unit 6, and displays a display of inquiring whether to end the measurement by setting the power of the ultrasonic imaging apparatus 8 to Off or to continue the measurement of the operator, on the display unit 6.

In a case where the operator selects to set the power to Off, and the shooting end signal S22 is received from the operation unit 4, it is determined that the shooting end instruction is received (Yes in S109), the control computation unit 3 sets the power of the ultrasonic imaging apparatus 8 to Off and ends the processing.

On the other hand, in a case where the operator selects to set the power to Off, and a shooting continuation signal S23 indicating a shooting continuation instruction is received from the operation unit 4, it is determined that the shooting end instruction is not received (No in S109), the processing returns to Step S102, and a set of measurement is repeated.

The control computation unit 3 may add Step S110 (not illustrated) of displaying a part or all of the image information items S4 to S7 on the display unit 6, and then, of displaying a display of inquiring whether or not to continue the processing of the operator, during each of the steps of Steps S104 to S107 or between the respective steps.

In this case, when the operator selects not to continue the processing through the operation unit 4, the control computation unit 3 may change a part of the processing or the entire processing in the near step such as Step S102 in Steps S103 to S107, or the operator may change the state of the subject 7, and then, the processing may return to any step before Steps S102 to S107, and a part or all of Steps S102 to S107 may be executed again. At this time, a parameter relevant to a change in the processing of each step may be input by the operator through the operation unit 4, or may be set in advance and may be changed according to a change protocol stored in the storage unit 5.

On the other hand, in a case where the operator selects to continue the processing through the operation unit 4, the control computation unit 3 executes the next step. By adding such Step S110, it is possible for the operator to confirm whether or not to shoot a desired image, and for example, it is possible to omit a step which is not necessary for a case where the subject 7 is not correctly set, and the subject structure image S4 and (or) the state information S6 are not capable of being correctly acquired.

In addition, the control computation unit 3 may repeat each of Steps S102 to S108 a predetermined number of times.

Figure 7:
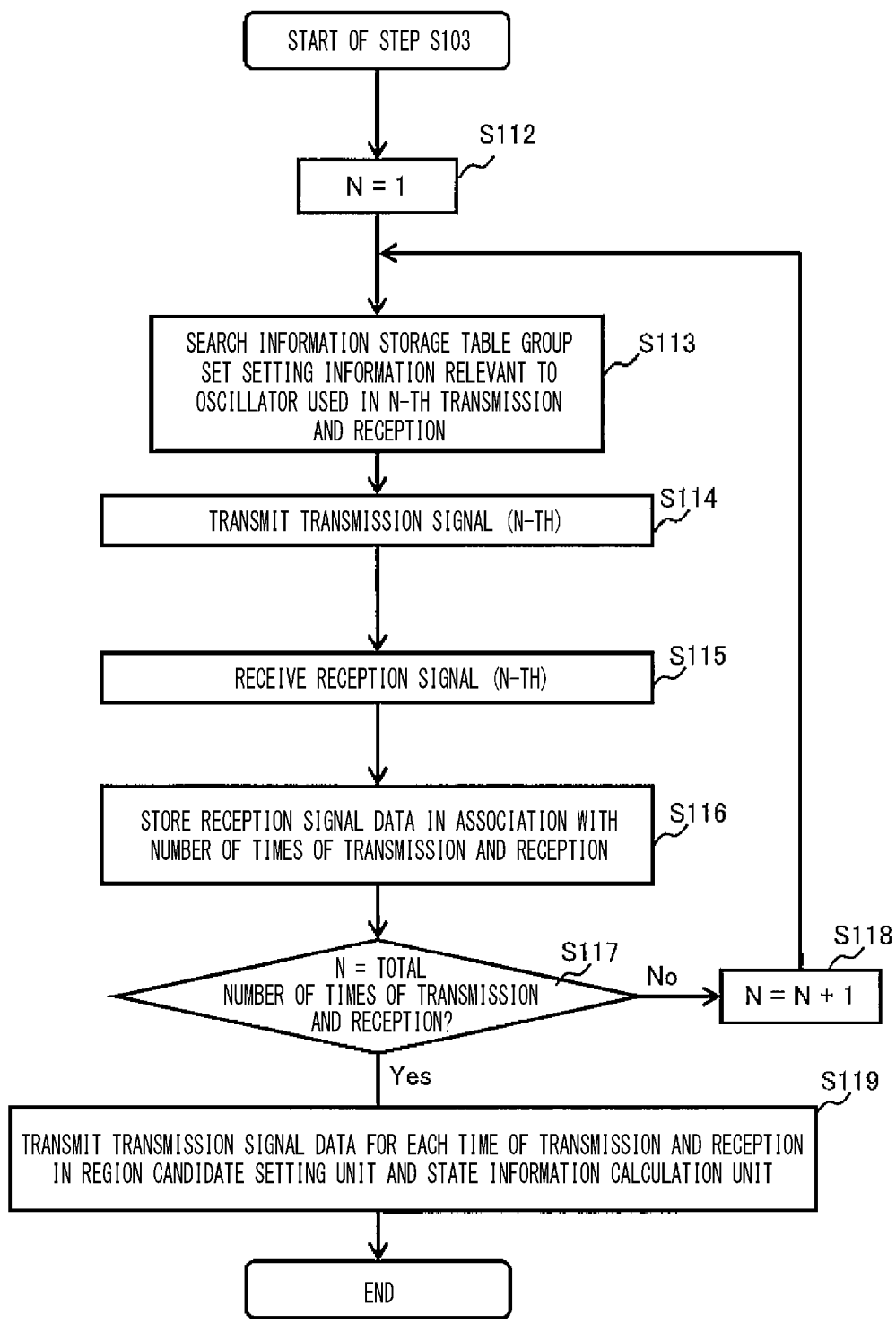
FIG. 7 is an example of a flowchart illustrating an operation of a transmission and reception signal control unit.

FIG. 7 is an example of a flowchart illustrating the operation of the transmission and reception signal control unit 10. The transmission and reception signal control unit 10 sets the number of times of transmission and reception N=1 (S112), searches the information storage table group 100 of FIG. 4, stored in the storage unit 5, and sets (stores) the setting information relevant to the oscillator 1 used in the first transmission and reception in a storage unit (not illustrated) of the transmission and reception signal control unit 10 (S113). Specifically, the transmission and reception signal control unit 10 searches the information storage table group 100, specifies an entry in which the number of times of transmission 111 and the number of times of reception 121 are "1", and reads out and sets a value stored in the oscillators 112 and 122, the apodizations 114 and 124, and the delay time 115, in which the switches 113 and 123 are set to "ON", in the transmission and reception setting information S8 stored in each specified entry.

According to such setting, the transmission and reception signal control unit 10 transmits the transmission signal S1 to the oscillators 1a to 1c (S114), and transmits the first ultrasonic wave to the oscillator array 2. Next, in a case where the first reception signal S2 is received from all of the oscillators 1 (1a to 1x) (S115), the transmission and reception signal control unit 10 stores a part of the reception signal S2 or the entire reception signal S2 in the transmission and reception signal control unit 10 in association with the number of times of transmission and reception N, as the reception signal data S3 (S116).

Next, the transmission and reception signal control unit 10 compares the number of times of transmission and reception N=1 with the total number of times of transmission and reception set in Step S111, and determines whether or not the number of times of transmission and reception N=1 reaches the total number of times of transmission and reception (S117). In a case where the number of times of transmission and reception N=1 reaches the total number of times of transmission and reception (Yes in S117), the transmission and reception signal control unit 10 transmits the reception signal data S3 for each time of transmission and reception, stored in Step S116, to the region candidate setting unit 12 and the state information calculation unit 13 (S119), and ends the processing. The control computation unit 3 proceeds to Step S104. Furthermore, the transmission and reception signal control unit 10 may transmit the reception signal data S3 for each time of transmission and reception to the storage unit 5, and may store the reception signal data S3 in the storage unit 5.

On the other hand, in a case where the number of times of transmission and reception N=1 does not reach the total number of times of transmission and reception (No in S117), the transmission and reception signal control unit 10 adds 1 to N (increases N) (S118) to be N=2, returns to Step S113, and executes the steps after Step S113. That is, the transmission and reception signal control unit 10 transmits the transmission signal S1 to the oscillators 1d to 1f (S114), receives the second reception signal S2 from all of the oscillators 1 (1a to 1x) (S115), and stores the second reception signal S2 in association with the number of times of transmission and reception N, as the reception signal data S3 (S116). After that, the transmission and reception signal control unit 10 repeats Steps S113 to S118 until the number of times of transmission and reception N reaches the total number of times of transmission and reception, which is set.

Figure 8:
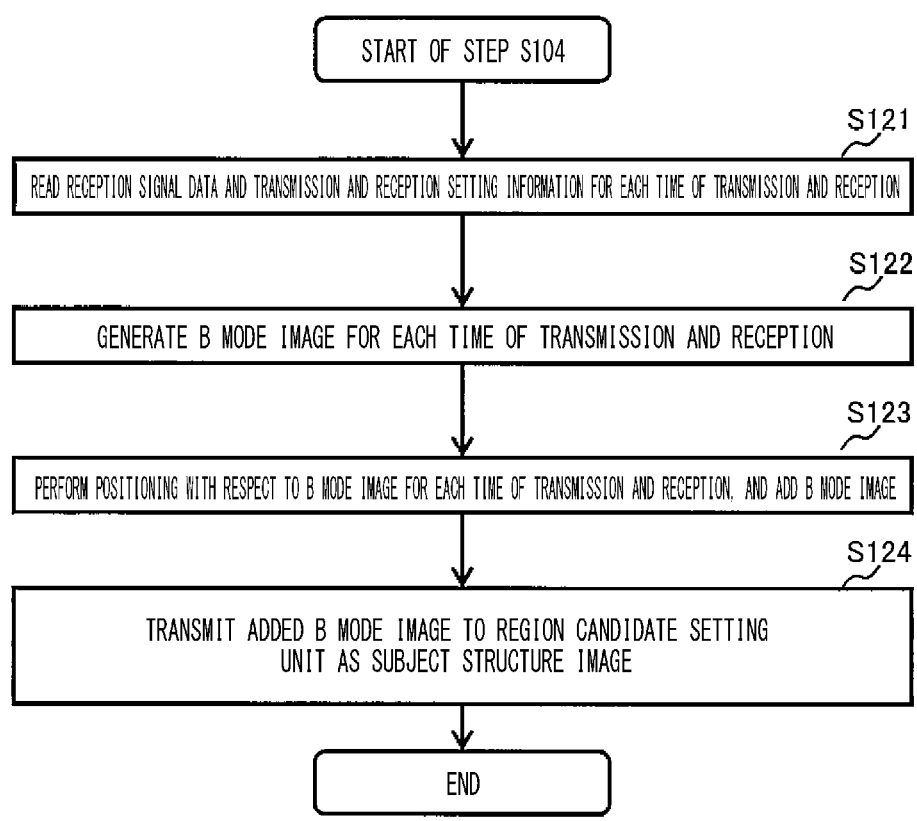
FIG. 8 is an example of a flowchart illustrating an operation of the structure image generating unit.

FIG. 8 is an example of a flowchart illustrating the operation of the structure image generating unit 11. An operation of generating the subject structure image S4 based on the reflection wave by the structure image generating unit 11 will be described by using FIG. 8.

The structure image generating unit 11 reads the reception signal data S3 and the transmission and reception setting information S8 (S121). Next, the structure image generating unit 11 performs the phasing addition processing for each time of transmission and reception on the basis of the reception signal data S3 for each time of transmission and reception, generates the B mode image (S122), positions the B mode image for each time of transmission and reception, and adds the B mode image (S123). Furthermore, in the generation of the B mode image in Step S122, for example, a known technology such as Non-Patent Document 2 may be used.

The structure image generating unit 11 transmits the added B mode image to the region candidate setting unit 12 as the subject structure image S4 (S124), and ends the processing. The control computation unit 3 proceeds to Step S105. Furthermore, the structure image generating unit 11 may transmit the subject structure image S4 to the storage unit 5, and may store the subject structure image S4 in the storage unit 5.

The subject structure image S4 may generate the B mode image by aperture synthesis in which the reception signal data items S3 of a different number of times of transmission and reception are added together at a time point of the reception signal S2, which is a radio frequency (RF) signal, without preparing the B mode image for each time of transmission and reception, and may use the B mode image as the subject structure image S4, may generate the B mode image on the basis of the reception signal data S3 of one time of transmission and reception, and may use the B mode image as the subject structure image S4, or may use a result of performing computation such as obtaining a correlation for each point and (or) a maximum value, with respect to a plurality of B mode images, as the subject structure image S4.

In addition, the subject structure image S4 may be an image based on the transmission wave. For example, the structure image generating unit 11 may generate a physical property value image reflecting a physical property value such as the acoustic velocity of the tissue calculated by the ultrasonic tomography method, the attenuation of the transmission signal intensity, and the hardness of the tissue, and may use the physical property value image as the subject structure image S4. Furthermore, in the generation of the physical property value image, for example, a known technology such as Non-Patent Document 2 may be used.

In addition, the subject structure image S4 may be a plurality of images but not one image, or may be a plurality of images relevant to a plurality of sectional surfaces. At this time, the plurality of images may be a plurality of subject structure images S4 imaged by different methods on the basis of the reception signal data S3 acquired by single transmission and reception setting information item S8, may be a plurality of subject structure images S4 imaged by the same method on the basis of the reception signal data S3 acquired by different transmission and reception setting information items S8, or may be a combination of two types of subject structure images S4.

Figure 9:
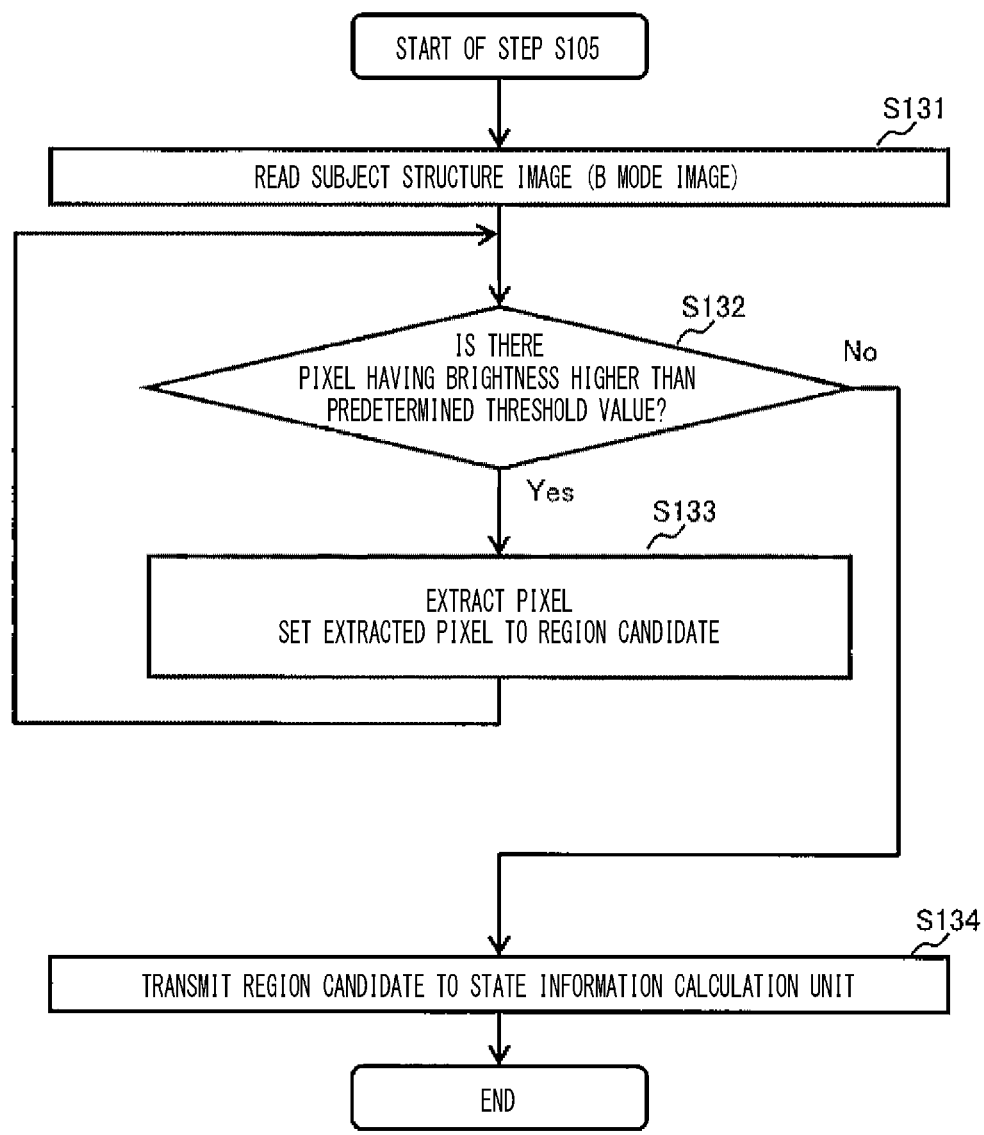
FIG. 9 is an example of a flowchart illustrating an operation of the region candidate setting unit.

FIG. 9 is an example of a flowchart illustrating the operation of the region candidate setting unit 12. An operation of setting the region candidate S5 based on the reflection wave by the region candidate setting unit 12 will be described by using FIG. 9. The region candidate setting unit 12 reads the subject structure image S4 (the B mode image) (S131). Next, the region candidate setting unit 12 determines whether or not there is a pixel having a brightness higher than a predetermined threshold value, in pixels in the read subject structure image S4 (S132). In a case where there is a pixel having a brightness higher than the predetermined threshold value (Yes in S132), the region candidate setting unit 12 extracts the pixel, sets the extracted pixel to be in the region candidate S5 (S133), returns to Step S132, and repeatedly executes Steps S132 and S133.

In Step S132, in a case where there is no pixel having a brightness higher than the predetermined threshold value (No in S132), the region candidate setting unit 12 transmits the region candidate S5 to the state information calculation unit (S134), and ends the processing. The control computation unit 3 proceeds to Step S106. Furthermore, the region candidate setting unit 12 may transmit the tissue region candidate S5 to the storage unit 5, and may store the tissue region candidate S5 in the storage unit 5.

Furthermore, in Step S134, in a case where there is no region candidate S5 transmitted to the state information calculation unit 13, the control computation unit 3 may return to the previous step (any one of Steps S102 to S104, S111 in FIG. 6), and may perform the measurement again. That is, in a case where the region candidate S5 is not capable of being set, the control computation unit 3 may perform the measurement again, and may set the region candidate S5. By performing the measurement again, it is possible to reduce useless processing, and to provide a more vivid image with respect to the operator.

The region candidate S5 may be one or a plurality of regions surrounded by a closed curve or a closed surface, or may be set for each element unit in an imaging space region such as a pixel or a voxel. A setting mode of the region candidate S5 is not limited to a mode of distinguishing the brightness of the subject structure image S4 as described above with a threshold value. For example, in the case of using the physical property value image, which is the subject structure image S4 based on the transmission wave, for example, a region having a large change in the physical property value may be set as the region candidate S5.

In addition, as described above, the region candidate setting unit 12 may automatically set the region candidate S5, on the basis of the subject structure image S4, and for example, may display the subject structure image S4 on the display unit 6, and may allow the operator to input a region, which is the subject structure image S4, to the operation unit 4, as the region candidate S5. In addition, the candidate setting unit 12 may set the region candidate S5 to be displayed on the display unit 6, and may allow the operator to further limit the region candidate S5 from the region candidate S5 through the operation unit 4.

The region candidate S5 is set on the basis of the subject structure image S4, and thus, it is possible to set the region candidate S5 from information with respect to the subject structure, and it is possible to decrease erroneous setting of a region other than a boundary or a tissue region, as the region candidate S5. Therefore, an effect of increasing accuracy and (or) reliability of the region candidate S5 or increasing accuracy and (or) reliability of the state information S6 can be obtained.

In addition, the region candidate setting unit 12 may set the region candidate S5 on the basis of the subject structure image S4, and image data acquired by different apparatuses. In addition, the region candidate setting unit 12 may set the region candidate S5 on the basis of information different from the subject structure image S4. For example, the region candidate setting unit 12 may set the region candidate S5 on the basis of the reception signal data S3. That is, the region candidate setting unit 12 may set a predetermined threshold value with respect to the reception signal data S3, and when the maximum value of the reception signal data S3 exceeds the threshold value, the entire region of the subject 7 may be set as the region candidate S5.

Here, an example of setting the region candidate S5 on the basis of the reception signal data S3 by the region candidate setting unit 12 will be described by focusing on points different from those of FIG. 9. In Step S131, the region candidate setting unit 12 reads the reception signal data S3 which is transmitted from the transmission and reception signal control unit 10. Next, in step 132, the region candidate setting unit 12 determines whether or not there is data having a size higher than a predetermined threshold value, in the read reception signal data S3.

In a case where there is a pixel having a size higher than the predetermined threshold value (Yes in S132), and in Step S133, the region candidate setting unit 12 extracts the data, sets a reflection point corresponding to the extracted data to the region candidate S5, returns to Step S132, and repeatedly executes Steps S132 and S133.

The region candidate S5 is set on the basis of the reception signal data S3, and thus, a process of generating the subject structure image S4 can be omitted, and therefore, it is possible to perform the computation with a smaller amount of computation and a smaller amount of memory, and to reduce time from the start of the imaging to the display of the state information S6.

Figure 10:
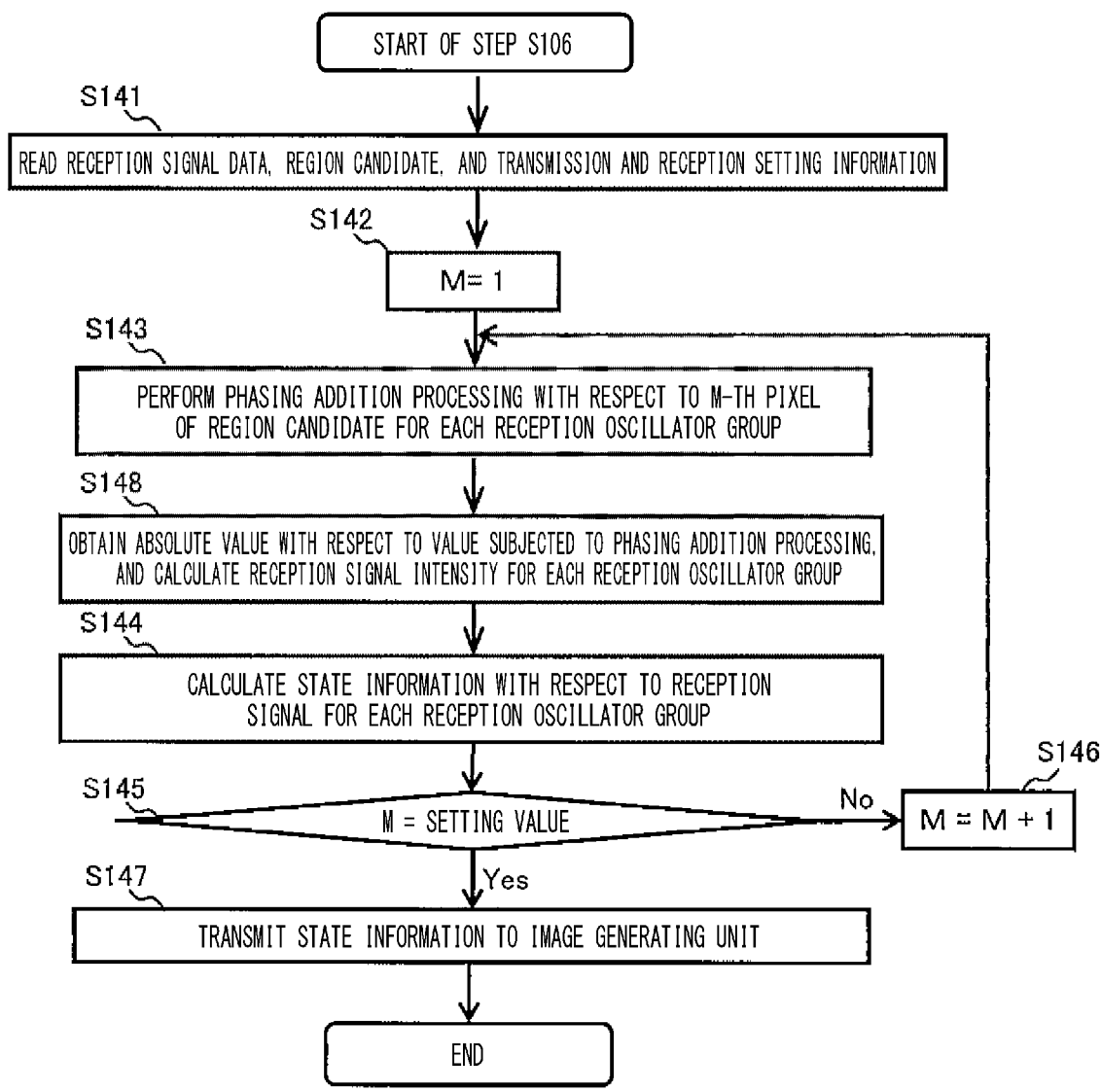
FIG. 10 is an example of a flowchart illustrating an operation of the state information calculation unit.

FIG. 10 is an example of a flowchart illustrating the operation of the state information calculation unit 13.

The state information calculation unit 13 reads the reception signal data S3, the region candidate S5, and the transmission and reception setting information S8 (S141). Next, the state information calculation unit 13 sets a pixel number M=1 (S142), and performs the phasing addition processing with respect to the reception signal data S3 on the basis of the reception signal data S3 and the transmission and reception setting information S8, with respect to a pixel of the pixel number M=1, in the region candidate S5 (S143). Specifically, the state information generating unit 13 divides all of the oscillators 1 receiving the ultrasonic wave into one or more reception oscillator groups, and performs the phasing addition processing with respect to the reception signal data S3 which is received by the oscillator 1 included in the reception oscillator group, for each of the reception oscillator groups, on the basis of the reception signal data S3 and the transmission and reception setting information S8 which are received by the oscillator 1 included in the reception oscillator group. Furthermore, each of the reception oscillator groups is configured of one or more oscillators 1.

Then, the state information calculation unit 13 obtains an absolute value with respect to the value of the reception signal data subjected to the phasing addition processing for each of the reception oscillator groups, and calculates a reception signal intensity for each of the reception oscillator groups in the pixel of M=1 (S148). At this time, the absolute value is not simply obtained, but an envelope curve of the reception signal data subjected to the phasing addition processing is obtained, and thus, the reception signal intensity for each of the reception oscillator groups may be obtained.

The state information calculation unit 13 performs predetermined computation with respect to the reception signal intensity for each of the reception oscillator groups, and calculates an index value, which is a result thereof, as the state information S6 (S144). The index value, for example, includes a difference between a variance value or a maximum value and a minimum value, and the like.

Next, the state information calculation unit 13 compares the pixel number M=1 with a predetermined setting value, and determines whether or not the pixel number M=1 reaches the setting value (S145). In a case where the pixel number M=1 does not reach the setting value (No in S145), the state information calculation unit 13 adds 1 to M (increases M) (S146) to be M=2, returns to Step S143, and executes the steps after Step S143.

Here, the predetermined setting value may be a value obtained from the number of pixels in the region candidate S5 read in Step S141, or may be a value set by the transmission and reception setting information S8.

After that, the state information calculation unit 13 repeats Steps S143 to S146 until a pixel number M reaches the setting value, and calculates the state information S6 with respect to all pixels in the region candidate S5.

On the other hand, in a case where the pixel number M reaches the setting value (Yes in S145), the state information calculation unit 13 transmits the state information S6 calculated for each of the pixel numbers M to the image generating unit 14 (S147), and ends the processing. The control computation unit 3 proceeds to Step S107. Furthermore, the state information calculation unit 13 may transmit the state information S6 and the pixel number M in association with each other to the storage unit 5, and may store the state information S6 and the pixel number M in the storage unit 5. In this case, the state information S6 for each of the pixel numbers is stored in the storage unit 5.

The state information may be calculated by performing the phasing addition processing for each time of transmission and reception as described above, and by performing predetermined computation with respect to the value of the reception signal intensity subjected to the phasing addition processing.

In the case of the state information based on the reflection wave, any state information may be used insofar as reflection properties of a certain region in the region candidate S5 can be obtained. For example, any feature amount (any amount of statistics) may be calculated from the intensity distribution of the reception signal S2 for each of the oscillators 1 receiving the reception signal S2 of a certain number of times of transmission and reception.

Here, the intensity distribution is a correspondence relationship between the oscillator 1 and the intensity of the reception signal S2 received by the oscillator 1 (the reception signal intensity), or a correspondence relationship between the oscillator 1 to which the ultrasonic wave is transmitted, and the intensity of the reception signal S2 received on the basis of the ultrasonic wave (the reception signal intensity).

In the case of the state information based on the transmission wave, any state information may be used insofar as a physical property value of a certain region in the region candidate S5 can be obtained. For example, the acoustic velocity and (or) the attenuation may be calculated by using the ultrasonic tomography method.

The state information may be state information with respect to one sectional surface, or may be state information relevant to a plurality of sectional surfaces. In this case, the state information calculation unit 13 may calculate the state information S6 for each of the sectional surfaces, and may calculate the state information S6 by computing the entire at one time.

Figure 11:
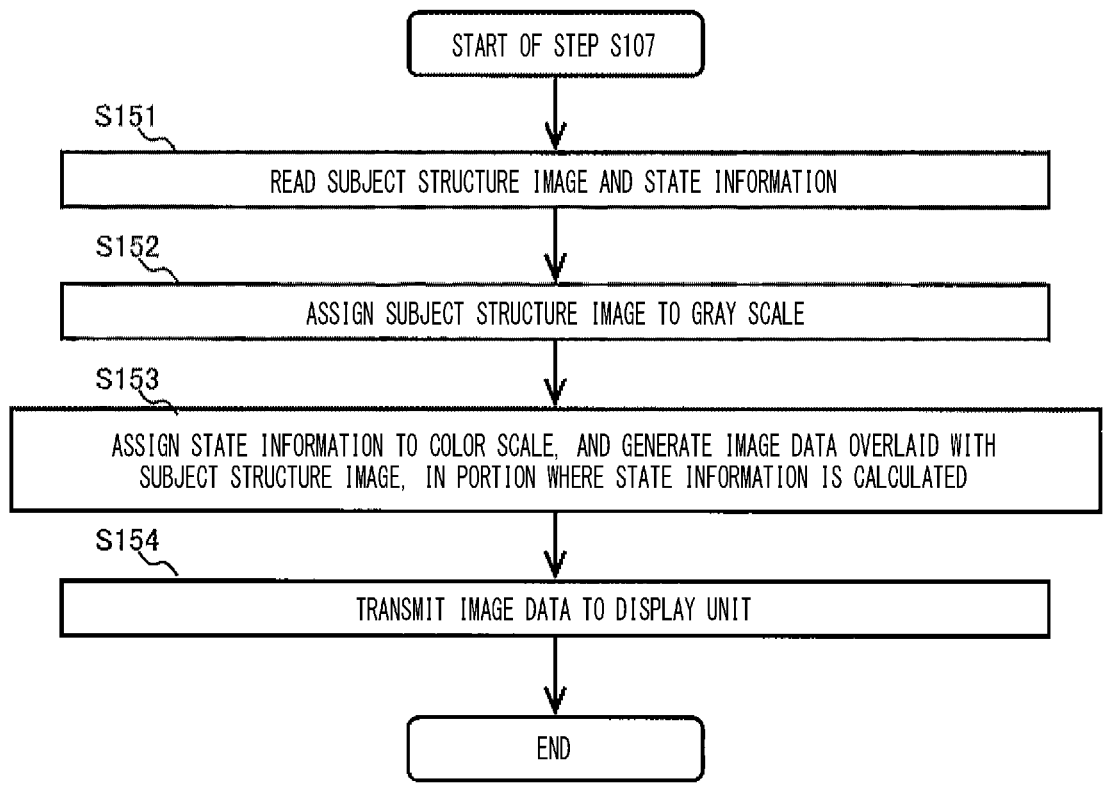
FIG. 11 is an example of a flowchart illustrating an operation of the image generating unit.

FIG. 11 is an example of a flowchart illustrating the operation of the image generating unit 14. The image generating unit 14 reads the subject structure image S4 and the state information S6 (S151). Next, the image generating unit 14 assigns the subject structure image S4 to a gray scale (S152), and assigns the state information S6 to a color scale, with respect to a portion in which the state information S6 is calculated (a pixel in which the state information S6 exists), that is, the pixel of the region candidate S5, generates the image data S7 which is overlaid on the subject structure image S4 to be synthesized (S153), transmits the image data S7 to the display unit 6 (S154), and ends the processing. The control computation unit 3 proceeds to Step S108. Furthermore, the image generating unit 14 may transmit the image data S7 to the storage unit 5, and may store the image data S7 in the storage unit 5.

As described above, the image data S7 may not overlay the subject structure image S4 on the state information S6, but may be in an aspect where it is possible to know which point of the state information S6 corresponds to which point of the subject structure image S4. For example, the image data S7 may arrange the state information S6 and the subject structure image S4 at the same reduced scale and in the same direction, or may alternately display the state information S6 and the subject structure image S4 on the display unit 6. In addition, the image data S7, for example, may only use state information having a value in a specific range, in the state information S6. Accordingly, it is possible for the operator to easily grasp state information in a range of a value of interest, in the state information S6.

In addition, the image generating unit 14 may generate the image data S7 on the basis of at least the state information S6, and may not use the subject structure image S4 which is used for setting the region candidate S5. In this case, the image generating unit 14 may generate the image data S7 by only using the state information S6, may newly generate an image relevant to the subject 7 from the reception signal data S3, and may generate the image data S7 by synthesizing an image in which the image and the subject structure image S4 are synthesized, and the state information S6. In addition, the image generating unit 14 may generate the image data S7 by using the state information S6 and (or) the subject structure image S4 relevant to a plurality of sectional surfaces. In this case, the image data S7 may be three-dimensional image data including a plurality of sectional surfaces.

As described above, according to this embodiment, the state information S6 is calculated in the region candidate S5 set on the basis of the reception signal data S3 acquired from the entire area of the subject 7, and thus, the state information S6 of the boundary of the tissue in the subject 7 and (or) the interior of the tissue can be calculated by a small amount of memory, compared to a case where the state information S6 is calculated from the reception signal data S3 of the entire area of the subject 7. That is, a region is set in which the state information S6 is calculated on the basis of the reception signal S2 of the ultrasonic wave, and thus, it is possible to reduce an amount of memory and (or) an amount of computation, which are necessary for the ultrasonic imaging apparatus 8, and to rapidly calculate the state information S6.

As a result thereof, it is possible to reduce calculation time of a measurement result per one subject, and thus, in an application such as examination, in which it is necessary to display the measurement result for a short period of time, it is possible to utilize the state information S6 of the ultrasonic imaging apparatus 8. That is, according to the ultrasonic imaging apparatus 8 of this embodiment, the state information, which is the measurement result of the subject 7, can be displayed for a short period of time, and thus, in the examination or the like, it is possible to view the ultrasonic image reflecting the state information for a short period of time after shooting the subject. In addition, it is possible to reduce time for constraining the subject in order for the examination. In addition, it is possible to confirm whether or not to correctly image a portion of interest in which detailed examination is required at the time of the examination, and in a case where the portion of interest is not capable of being correctly imaged, it is possible to image again the portion of interest on the spot, and it is not necessary to call the subject at another time in order to image again the portion of interest.

In addition, in general, a size and a shape of a tissue of a growth or the like in the subject 7, a position of the tissue in the subject 7, and the like are not capable of being predicted in advance. The ultrasonic imaging apparatus 8, which is an ultrasonic CT apparatus, is capable of receiving the ultrasonic wave having an interaction with the subject 7 (the ultrasonic wave reflecting the tissue state information of the subject 7) from various angles (for example, a multidirection such as 360 degrees), with respect to the ultrasonic wave transmitted to the subject 7. That is, the ultrasonic imaging apparatus 8 is capable of acquiring a lot of information of the subject 7 relevant to an angle of receiving the ultrasonic wave the transmitted ultrasonic wave. For this reason, the ultrasonic imaging apparatus 8 is effective in imaging the tissue in the subject 7 in which the size, the shape, and the like are not capable of being predicted in advance, and it is possible to automatically set the region candidate of the tissue in the subject 7 on the basis of the received ultrasonic wave.

In addition, the ultrasonic imaging apparatus 8 generates an ultrasonic image on the basis of the ultrasonic wave received from various angles, and thus, it is possible to more accurately generate a vivid image, compared to an ultrasonic image of the related art. For this reason, in a case where the operator inputs the region candidate, the operator is capable of determining the region candidate on the basis of more accurate and vivid ultrasonic image of the ultrasonic imaging apparatus 8, and is capable of decreasing a load on the operator at the time of reading the ultrasonic image.

In general, in a case where a high ultrasonic reflector, a high attenuator, and the like, such as a bone, a tumor mass, and a gaseous body, exist in the subject 7, the reflection signal of the ultrasonic wave is not capable of being obtained from a region in the rear of the high ultrasonic reflector, the high attenuator, and the like, with respect to the oscillator 1 transmitting and receiving the ultrasonic wave. By changing a positional relationship and (or) an angle relationship between the oscillator 1 and the high ultrasonic reflector, the high attenuator, and the like, it is possible to change a region, which is a shadow of the high ultrasonic reflector, the high attenuator, and the like, but the region is not capable of being eliminated insofar as the high reflector, the high attenuator, and the like exist in a shooting (an imaging) space region (an imaging region), and thus, a region is generated in which the subject information is lacked. The ultrasonic imaging apparatus 8, which is an ultrasonic CT apparatus, is capable of transmitting the ultrasonic wave to the subject 7 from various angles, and is capable of receiving the ultrasonic wave having an interaction with the subject 7 from various angles.

That is, in the ultrasonic imaging apparatus 8, a plurality of different images of the region, which is the shadow of the high ultrasonic reflector, the high attenuator, and the like, can be synthesized in one image, and thus, the subject information with respect to the entire region of the subject 7 can be obtained. In the ultrasonic imaging apparatus 8, the region candidate S5 can be set on the basis of the subject information with respect to the entire region of the subject 7. That is, even in a case where there are the high ultrasonic reflector, the high attenuator, and the like, the ultrasonic imaging apparatus 8 is effective in imaging the tissue of the entire region in the subject 7, and is capable of setting the region candidate S5 of the tissue in the subject 7 on the basis of the received ultrasonic wave.

Modification Example 1-1

Next, Modification Example 1-1 of the first embodiment will be described. FIG. 12 is a diagram illustrating Modification Example 1-1 of a calculation method of the state information S6 based on the reflection wave. In this modification example, the ultrasonic imaging apparatus 8 performs transmission and reception of the ultrasonic wave a plurality of times, and at this time, the oscillator 1 transmitting the ultrasonic wave is changed, and the oscillator 1, which is a part of the plurality of oscillators 1, receives the reflection wave, and thus, the reflection properties of the ultrasonic wave are measured.

The case of identifying the rough boundary and the smooth boundary in the subject 7 illustrated in FIG. 2A will be described as an example, by focusing on a point that the operations of the transmission, the reception signal control unit 10, the state information calculation unit 13, and the oscillator array 2 are different, compared to the first embodiment described above. In this modification example, the oscillator array 2 includes at least two oscillators 1.

Figure 12A:
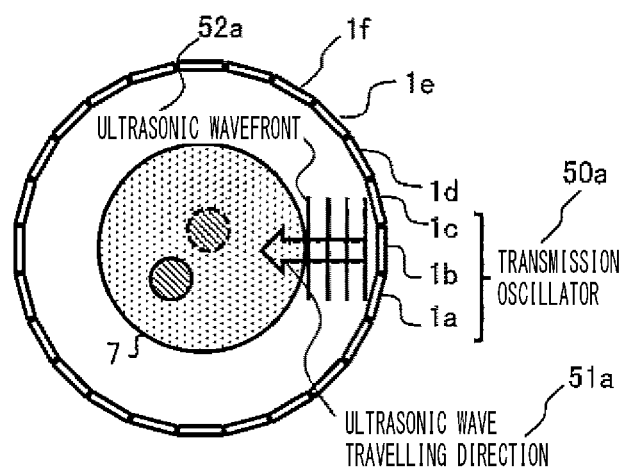
FIG. 12A is a diagram illustrating an example of the N=1-th transmission aspect of the ultrasonic signal in Modification Example 1-1.
Figure 12B:
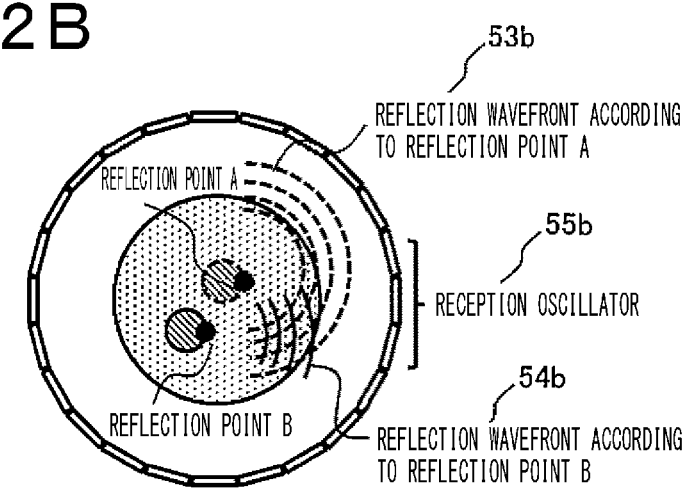
FIG. 12B is a diagram illustrating an example of the N=1-th reception aspect of the ultrasonic signal.
Figure 12C:
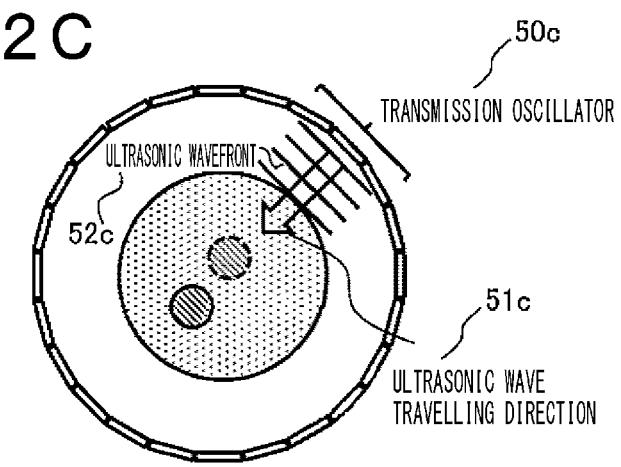
FIG. 12C is a diagram illustrating an example of the N=2-th transmission aspect of the ultrasonic signal.
Figure 12D:
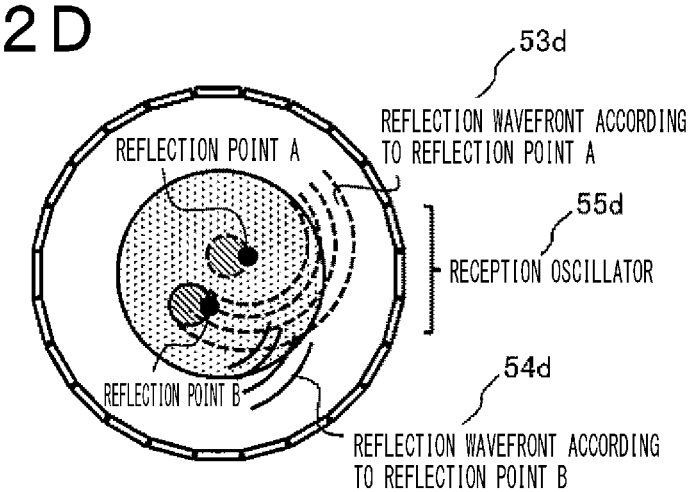
FIG. 12D is a diagram illustrating an example of the N=2-th reception aspect of the ultrasonic signal.
Figures 12E, 12F, 13A:
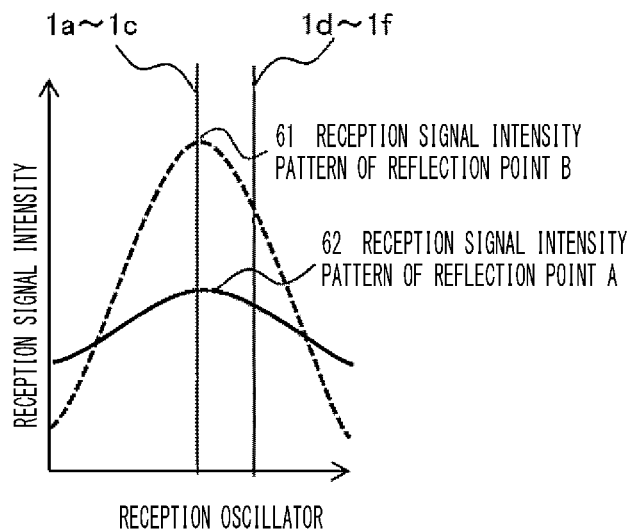
FIG. 12E is a diagram illustrating an example of graph illustrating a reception signal intensity of a reflection wave.
FIG. 12F is a diagram illustrating an example of a part of transmission and reception setting information.
FIG. 13A is a diagram illustrating an example of a part of transmission and reception setting information, in Modification Example 1-2.

FIG. 12F is a diagram illustrating an example of a part of the transmission and reception setting information S8, and is a diagram illustrating an example of a relationship between the oscillator 1 transmitting the ultrasonic wave for each time of transmission and reception 70 of the ultrasonic wave (a transmission oscillator 50) and the oscillator 1 receiving the ultrasonic wave (a reception oscillator 55). In the first transmission and reception 70 and the second transmission and reception 70, the transmission oscillators 50 are different, but the reception oscillators 55 are the same.

The transmission and reception signal control unit 10 changes the transmission oscillator 50 in Step S114 of FIG. 7, according to the number of times of transmission and reception N, that is, changes the oscillator 1, which is an address to which the transmission signal S1 is transmitted, and thus, a sending position of the ultrasonic wave and an ultrasonic wave travelling direction are changed, and the reflection properties of the ultrasonic wave are measured.

The control computation unit 3 sets the number of times of transmission and reception to a plurality of times of greater than or equal to 2, according to the transmission and reception setting information S8 of FIG. 12F, in Step S111 of FIG. 6.

FIG. 12A is a diagram illustrating an example of the N=1-th transmission aspect of the ultrasonic signal. The transmission and reception signal control unit 10 transmits the transmission signal S1 to the oscillators 1a to 1c, which are a transmission oscillator 50a, in the oscillators 1 configuring the oscillator array 2 in Step S114 of FIG. 7. The oscillators 1a to 1c receiving the transmission signal S1, send the ultrasonic wave towards the subject 7, as illustrated in an ultrasonic wave travelling direction 51a. In FIG. 12A, a transmitted ultrasonic wavefront 52a configures a plane wave, but this is an example, and the ultrasonic wavefront may be in the shape of being diffused, or may be in the shape of being focused.

FIG. 12B is a diagram illustrating an example of the N=1-th reception aspect of the ultrasonic signal. In the N=1-th transmission of the ultrasonic signal, a reflection wave reflected on a reflection point A and a reflection point B, illustrated in FIG. 12B, are respectively propagated through the oscillator array 2 by reflection wavefronts 53b and 54b, in the subject 7. The reflection point A is a part of a rough boundary, and thus, the reflection wavefront 53b according to the reflection point A has comparatively low directionality. On the other hand, the reflection point B is a part of a smooth boundary, and thus, the reflection wavefront 54b according to the reflection point B has comparatively high directionality.

The transmission and reception signal control unit 10 sets the oscillators 1a to 1c, which are a reception oscillator 55b, to be effective, in the oscillators 1 configuring the oscillator array 2, at the time of receiving the N=1-th reception signal S2, that is, in Step S115 of FIG. 7, and in Step S116, stores the reception signal S2 of the oscillators 1a to 1c, as the reception signal data S3.

FIG. 12C is a diagram illustrating an example of the N=2-th transmission aspect of the ultrasonic signal. The transmission and reception signal control unit 10 transmits the transmission signal S1 to the oscillators 1d to 1f, which are a transmission oscillator 50c, and thus, the ultrasonic wave is transmitted in a direction illustrated in an ultrasonic wave travelling direction 51c from the oscillators 1d to 1f.

At this time, the ultrasonic wave travelling direction 51c of the transmitted ultrasonic wave is different from the N=1-th ultrasonic wave travelling direction 51a.

FIG. 12D is a diagram illustrating an example of the N=2-th reception aspect of the ultrasonic signal. In the N=2-th transmission of the ultrasonic signal, the reflection waves reflected on the reflection point A and the reflection point B, illustrated in FIG. 12D, are respectively propagated through the oscillator array 2 by reflection wavefronts 53d and 54d, in the subject 7. The sending position of the transmitted ultrasonic wave (the transmission oscillators 50a and 50c) and the ultrasonic wave travelling directions 51a and 51c are different for each time of transmission, and thus, the reflection direction of the ultrasonic wave, the reception signal intensity of the reflection wave, and the like at the reflection points A and B, are changed for each time of reception.

The transmission and reception signal control unit 10 performs the same operation as the N=1-th operation, at the time of receiving the N=2-th reception signal S2, that is, in N=2-th Step S115.

FIG. 12E is a diagram illustrating an example of a graph illustrating the reception signal intensity of the reflection wave from the reflection points A and B. A horizontal axis is the transmission oscillator, and a vertical axis is the reception signal intensity. As illustrated in FIG. 12E, when the ultrasonic wave is transmitted in Step S114 of FIG. 7, in a case where the effective oscillator 1 transmitting the ultrasonic wave is changed, according to "ON" of the switch 113, set in Step S113, a reception signal intensity pattern of the ultrasonic wave reflected on each of the reflection points (a reception signal intensity distribution) is changed according to a boundary state. Specifically, in the position of the oscillators 1a to 1c, a reception signal intensity pattern 61 of the reflection point B is formed into a sharp pointed shape, and a reception signal intensity pattern 62 of the reflection point A is formed into a gentle shape.

For example, in a case where the reception signal intensities from each of the reflection points are dispersed, a variance value increases at a reflection point having high directionality, and the variance value decreases at a reflection point having low directionality. The directionality of the reflection wave corresponds to the boundary state of the reflection point, and thus, for example, the variance value calculated in the procedure as described above may be used as an index value of the state information S6 based on the reflection wave. In this case, the state information calculation unit 13 performs the phasing addition processing for each time of transmission and reception, instead of the phasing addition processing for each of the reception oscillator groups, in Step S143 of FIG. 10. In addition, the state information calculation unit 13 performs predetermined computation with respect to the reception signal intensity subjected to the phasing addition processing for each time of transmission and reception, instead of the predetermined computation with respect to the reception signal intensity subjected to the phasing addition processing for each of the reception oscillator groups, in Step S144.

In addition, the state information calculation unit 13, calculates the variance value of the reception signal intensity subjected to the phasing addition processing for each time of transmission and reception, for each of the pixels, and calculates the state information S6, in the predetermined computation of Step S144.

As described above, according to Modification Example 1-1, a part of the oscillators 1 receives the ultrasonic wave, and thus, it is possible to decrease the amount of reception signal data S3 for each time of transmission and reception of the ultrasonic wave, to calculate the state information S6 with a smaller amount of memory and a smaller amount of computation, and to more rapidly calculate the state information S6.

In addition, the state information S6 may be calculated on the basis of the reception signal S2 at the time of changing the transmission oscillator 50. For example, the state information calculation unit 13 may calculate any one of the variance value standardized by the average value, a difference between the maximum value and the minimum value, and the like, with respect to the reception signal intensity subjected to the phasing addition processing, in Step S144 of FIG. 10.

In addition, for example, the state information calculation unit 13 may calculate an average value of phases of the reception signal S2 with respect to the N-th pixel of the region candidate S5 for each time of transmission and reception, instead of the phasing addition processing, in Step S143, and may calculate a dispersion of the average value of the phases, in Step S144, and thus, may calculate the state information S6.

As described in this modification example, the state information S6 may discriminate the roughness of the boundary surface of the tissue (for example, a growth), may be an index identifying a scattering body having a size less than or equal to a wavelength of an ultrasonic wave to be transmitted, and a boundary surface having a structure of a size greater than or equal to the wavelength of the ultrasonic wave to be transmitted, or may collectively identify them.

In addition, different setting values may be set to a voltage to be applied to the plurality of oscillators 1, delay time, and the like, and thus, a wavefront of the ultrasonic wave to be transmitted to the subject 7 may be changed, instead of changing the oscillator 1 effective in the transmission.

When the state information S6 is generated, the ultrasonic wave may be transmitted from the multidirection, and thus, the influence of the attenuation or the like on a propagation path of the received reflection from the reflection point to the oscillator 1 wave may be subtracted as a common component, and the state information S6 may be calculated with a higher accuracy.

Modification Example 1-2

Next, Modification Example 1-2 of the first embodiment will be described. FIG. 13 is a diagram illustrating Modification Example 1-2 of the calculation method of the state information S6 based on the reflection wave. In this modification example, the ultrasonic imaging apparatus 8 performs the transmission and reception of the ultrasonic wave a plurality of times, and at this time, the oscillator 1 receiving the reflection wave is changed, and thus, the reflection properties of the ultrasonic wave are measured.

The case of identifying the rough boundary and the smooth boundary in the subject 7 illustrated in FIG. 2A will be described as an example, by focusing on a point that the operations of the transmission and reception signal control unit 10, the state information calculation unit 13, and the oscillator array 2 are different, compared to Modification Example 1-1.

FIG. 13A is a diagram illustrating an example of a part of the transmission and reception setting information S8, and is a diagram illustrating an example of a relationship between the transmission oscillator 50 for each time of transmission and reception 70 of the ultrasonic wave and the reception oscillator 55. In the first transmission and reception 70 and the second transmission and reception 70, the transmission oscillators 50 are the same, but the reception oscillators 55 are different.

The transmission and reception signal control unit 10 changes the reception oscillator 55 in Step S115 of FIG. 7, that is, changes the oscillator 1 transmitting the reception signal S2 to the transmission and reception signal control unit 10, according to the number of times of transmission and reception N, and thus, a reception position of the ultrasonic wave, that is, a reception angle of the ultrasonic wave with respect to the ultrasonic wave travelling direction is changed, and the reflection properties of the ultrasonic wave are measured.

The control computation unit 3 sets the number of times of transmission and reception to a plurality of times of greater than or equal to 2, according to the transmission and reception setting information S8 of FIG. 13A, in Step S111 of FIG. 6.

In the N=1-th transmission of the ultrasonic signal, the transmission and reception signal control unit 10 transmits the transmission signal S1 to the oscillators 1a to 1c, which are the transmission oscillator 50, in the oscillators 1 configuring the oscillator array 2, in Step S114 of FIG. 7. The oscillators 1a to 1c receiving the transmission signal S1 send the ultrasonic wave towards the subject 7.

The transmission and reception signal control unit 10 sets the oscillators 1a to 1c, which are the reception oscillator 55, to be effective, in the oscillators 1 configuring the oscillator array 2, at the time of receiving the N=1-th reception signal S2, that is, in N=1-th Step S115, and in Step S116, stores the reception signal S2 from the oscillators 1a to 1c, as the reception signal data S3.

In the N=2-th transmission of the ultrasonic wave, the transmission and reception signal control unit 10 transmits the transmission signal S1 to the same oscillators 1a to 1c as the N=1-th transmission oscillator 50 in N=2-th Step S114. Therefore, the ultrasonic wave is transmitted from the oscillators 1a to 1c, and the sending position of the ultrasonic wave and the ultrasonic wave travelling direction are the same in the N=1-th transmission and the N=2-th transmission. Therefore, in the N=2-th transmission of the ultrasonic signal, the reflection wavefront of the ultrasonic wave reflected on the reflection point A and the reflection point B, illustrated in FIG. 12B in the subject 7, is not changed from the N=1-th transmission. The transmission and reception signal control unit 10 sets the oscillators 1d to 1f, which are the reception oscillator 55, to be effective, at the time of receiving the N=2-th reception signal S2, that is, in N=2-th Step S115, different from the N=1-th transmission, and in Step S116, stores the reception signal S2 of the oscillators 1d to 1f, as the reception signal data S3.

Figures 13B, 14A:
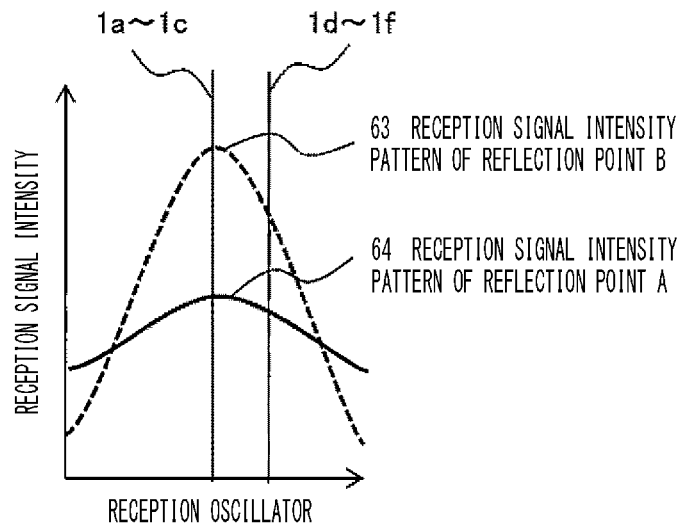
FIG. 13B is a diagram illustrating an example of a graph illustrating a reception signal intensity of a reflection wave.
FIG. 14A is a diagram illustrating an example of a part of transmission and reception setting information, in Modification Example 1-3.

FIG. 13B is a diagram illustrating an example of a graph illustrating the reception signal intensity of the reflection wave from the reflection points A and B. A horizontal axis is the reception oscillator, and a vertical axis is the reception signal intensity. As illustrated in FIG. 13B, in a case where the effective oscillator 1 receiving the ultrasonic wave is changed at the time of receiving the ultrasonic wave in Step S115, according to "ON" of the switch 123, set in Step S113 of FIG. 7, the reception signal intensity pattern ultrasonic wave reflected on each of the reflection points is changed according to the boundary state. Specifically, in the position of the oscillators 1a to 1c, a reception signal intensity pattern 63 of the reflection point B is formed into a sharp pointed shape, and a reception signal intensity pattern 64 of the reflection point A is formed into a gentle shape.

Therefore, as with Modification Example 1-1, the variance value of the reception signal intensity from each of the reflection points may be used as the index value of the boundary state information S6. In this case, as with Modification Example 1-1, the state information calculation unit 13 calculates the variance value of the reception signal intensity subjected to the phasing addition processing for each time of transmission and reception, for each of the pixels, and calculates the state information S6.

As described above, according to Modification Example 1-2, the reception oscillator 55 is changed to receive the ultrasonic wave without changing the transmission oscillator 50 for each time of transmission and reception of the ultrasonic wave, and thus, it is possible to decrease the amount of reception signal data S3 for each time of transmission and reception of the ultrasonic wave, to calculate the state information S6 with a smaller amount of memory and a smaller amount of computation, and to more rapidly calculate the state information S6.

In addition, the state information S6 may be calculated on the basis of the reception signal S2 at the time of changing the reception oscillator 55, and as with Modification Example 1-1, may calculate any one of the variance value standardized by the average value, a difference between the maximum value and the minimum value, and the like, with respect to the reception signal intensity subjected to the phasing addition processing.

In addition, as with Modification Example 1-1, the average value of the phases with respect to the N-th pixel of the region candidate S5 may be calculated for each time of transmission and reception, and the dispersion of the average value of the phases may be calculated, and thus, the state information S6 may be calculated.

In addition, as with Modification Example 1-1, the state information S6 may discriminate the roughness of the boundary surface, may be the index identifying the scattering body and the boundary surface, or may collectively identify them.

In addition, when the state information S6 is calculated, the ultrasonic wave reflected on the subject 7 is received from the multidirection, and thus, the influence of the attenuation or the like on the propagation path of the ultrasonic wave from the transmission oscillator 50 to the reflection point may be subtracted as the common component, and the state information S6 may be calculated with a higher accuracy.

Modification Example 1-3

Next, Modification Example 1-3 of the first embodiment will be described. FIG. 14 is a diagram illustrating Modification Example 1-3 of the calculation method of the state information S6 based on the reflection wave. In this modification example, the ultrasonic imaging apparatus 8 performs the transmission and reception of the ultrasonic wave a plurality of times, and at this time, a correspondence relationship between the oscillator 1 transmitting the ultrasonic wave and the oscillator 1 receiving the reflection wave is changed (switched), and thus, the reflection properties of the ultrasonic wave are measured.

The case of identifying the rough boundary and the smooth boundary in the subject 7 illustrated in FIG. 2A will be described as an example, by focusing on a point that the operations of the transmission and reception signal control unit 10, the state information calculation unit 13, and the oscillator array 2 are different, compared to Modification Example 1-1.

In this modification example, the transmission and reception signal control unit 10 switches a correspondence relationship between the transmission oscillator 50 and the reception oscillator 55, according to the number of times of transmission and reception N, and thus, receives a lot of reception signals S2 based on the reflection wave from each of the reflection points of the subject 7, and the state information calculation unit 13 calculates the state information S6 on the basis of the obtained reception signal data S3.

FIG. 14A is a diagram illustrating an example of a part of the transmission and reception setting information S8, and a diagram illustrating an example of a relationship between the transmission oscillator 50 for each time of transmission and reception 70 of the ultrasonic wave and the reception oscillator 55. As illustrated in FIG. 14A, in a case where all of the ultrasonic waves from the same transmission oscillator are received by the reception oscillator 55, the transmission and reception signal control unit 10 changes the transmission oscillator 50, and continues the transmission of the ultrasonic wave.

The control computation unit 3 sets the number of times of transmission and reception to a plurality of times of greater than or equal to 2, according to the transmission and reception setting information S8 of FIG. 14A, in Step S111 of FIG. 6. Furthermore, in FIG. 14A, an example is illustrated in which the oscillators 1a to 1c, which are the transmission oscillator 50, completely receive the ultrasonic wave to be transmitted a plurality of times, after all of the oscillators 1 configuring the oscillator array 2 sequentially become the reception oscillator 55, and then, change the transmission oscillator 50 to the oscillators 1d to 1f, completely receive the ultrasonic wave transmitted a plurality of times from the oscillators 1d to 1f, which are the transmission oscillator 50 after being changed, after all of the oscillators 1 sequentially become the reception oscillator 55, and such processing is repeated, and thus, all of the oscillators 1 sequentially become the transmission oscillator 50, but a transmission order and a reception order of the oscillators 1 are not limited insofar as all of the oscillators 1 become the transmission oscillator 50, and all of the oscillators 1 become the reception oscillator 55.

The transmission and reception signal control unit 10 transmits the transmission signal S1 to the oscillator 1 of the transmission oscillator 50 illustrated in FIG. 14A, in the oscillators 1 configuring the oscillator array 2, in Step S114 of each time of transmission and reception. The oscillator 1 of the transmission oscillator 50 receiving the transmission signal S1 sends the ultrasonic wave towards the subject 7.

The transmission and reception signal control unit 10 sets the oscillator 1 of the reception oscillator 55 illustrated in FIG. 14A to be effective, in Step S115 of each time of transmission and reception, in the oscillators 1 configuring the oscillator array 2, and in Step S116, stores the reception signal S2 from the effective oscillator 1 of the reception oscillator 55, as the reception signal data S3.

Figure 14B:
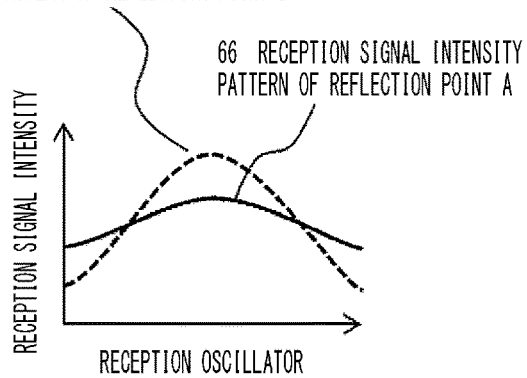
FIG. 14B is a diagram illustrating an example of a graph illustrating a reception signal intensity of a reflection wave in a case where oscillators $1a$ to $1c$ are a transmission oscillator.

FIG. 14B is a diagram illustrating an example of a graph illustrating the reception signal intensity of the reflection wave from the reflection points A and B in a case where the oscillators 1a to 1c are the transmission oscillator 50. That is, the reception signal intensity illustrated in FIG. 14B is a reception signal intensity in a case where the transmission and reception signal control unit 10 drives the oscillators 1a to 1c, which are the transmission oscillator 50 (sets the oscillators 1a to 1c to be effective) to transmit the ultrasonic wave, and all of the oscillators 1 receive the ultrasonic signal reflected on the reflection points A and B after all of the oscillators 1 sequentially become the reception oscillator 55.

Figure 14C:
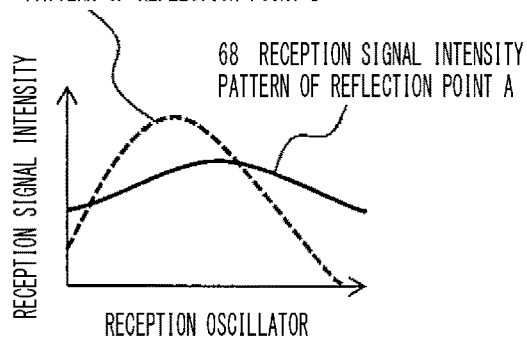
FIG. 14C is a diagram illustrating an example of a graph illustrating a reception signal intensity of a reflection wave in a case where oscillators $1d$ to $1f$ are a transmission oscillator.

FIG. 14C is a diagram illustrating an example of a graph illustrating the reception signal intensity of the reflection wave from the reflection points A and B in a case where the oscillators 1d to 1f are the transmission oscillator 50. That is, the reception signal intensity illustrated in FIG. 14C is a reception signal intensity in a case where the transmission and reception signal control unit 10 drives the oscillators 1d to 1f, which are the transmission oscillator 50, to transmit the ultrasonic wave, and all of the oscillators 1 receive the ultrasonic signal reflected on the reflection points A and B, after all of the oscillators 1 sequentially become the reception oscillator 55.

In the reflection at a reflection point having low directionality, such as the reflection point A, a change in the reception signal intensity pattern decreases at the time of changing the transmission oscillator 50. For this reason, as illustrated in a reception signal intensity pattern 66 of the reflection point A of FIG. 14B and a reception signal intensity pattern 68 of the reflection point A of FIG. 14C, the reception signal intensity pattern of the reflection point A has a high correlation or a high degree of similarity.

On the other hand, in the reflection at a reflection point having high directionality such as the reflection point B, the change in the reception signal intensity pattern increases as the transmission oscillator 50 is changed. For this reason, as illustrated in a reception signal intensity pattern 65 of the reflection point B of FIG. 14B and a reception signal intensity pattern 67 of the reflection point B of FIG. 14C, the reception signal intensity pattern of the reflection point B has a low correlation or a low degree of similarity.

According to the principle as described above, in this modification example, in the predetermined computation of Step S144 of FIG. 10, the state information calculation unit 13 generates the reception signal intensity pattern standardized by the maximum value of the reception signal intensity for each time of transmission and reception, in which the oscillators 1, which are the transmission oscillator 50, are the same, with respect to the reception signal intensity subjected to the phasing addition processing, calculates a correlation coefficient between the respective reception signal intensity patterns, and calculates the state information S6 based on the reflection wave.

In the example of FIG. 14, the reception signal intensity pattern 65 of the reflection point B and the reception signal intensity pattern 66 of the reflection point A are generated from the first transmission and reception 70 to the eighth transmission and reception 70, the reception signal intensity pattern 67 of the reflection point B and the reception signal intensity pattern 68 of the reflection point A are generated from the ninth transmission and reception 70 to the sixteenth transmission and reception 70, the correlation coefficient between the reception signal intensity pattern 65 and the reception signal intensity pattern 67 is calculated, and the correlation coefficient between the reception signal intensity pattern 66 and the reception signal intensity pattern 68 is calculated.

As described above, according to Modification Example 1-3, the correspondence relationship between the transmission oscillator 50 and the reception oscillator 55 is changed for each time of transmission and reception of the ultrasonic wave, and thus, it is possible to acquire a lot of information of the subject 7 relevant to an angle of receiving the ultrasonic wave with respect to the transmitted ultrasonic wave, compared to Modification Examples 1-1 and 1-2. In addition, according to Modification Example 1-3, for example, the reception oscillator in a position facing the transmission oscillator does not receive the signal, and thus, it is possible to decrease the amount of signal data S3 for each time of transmission and reception of the ultrasonic wave, to calculate the state information S6 with a smaller amount of memory and a smaller amount of computation, compared to the first embodiment, and to more rapidly calculate the state information S6.

In addition, the calculation of the correlation coefficient is not limited insofar as the state information S6 based on the reflection wave is calculated from the reception signal intensity patterns in which the oscillators 1, which are the transmission oscillator 50, are different. For example, in the predetermined computation of Step S144, the state information calculation unit 13 may calculate a difference between the respective reception signal intensity patterns, may calculate the dispersion thereof, and may calculate the state information S6.

In addition, as with Modification Examples 1-1 and 1-2, the state information S6 may discriminate the roughness of the boundary surface of the growth, may be an index identifying a scattering body having a size less than or equal to the wavelength of the ultrasonic wave to be transmitted, and a parenchyma (the tissue) having a size greater than or equal to the wavelength of the ultrasonic wave to be transmitted, or may collectively identify them.

In this modification example, the state information S6 is calculated on the basis of the standardized reception signal intensity pattern, and thus, it is possible to calculate the state information S6 based on the reflection wave without affecting the attenuation of the ultrasonic signal due to a change in the propagation path at the time of changing the oscillator 1 transmitting ultrasonic wave.

<Shape Example of Oscillator Array>

In the first embodiment, the oscillator array 2 may be configured to measure the reflection properties of the ultrasonic wave transmitted from the oscillator 1, and the arrangement of the oscillators 1 in the oscillator array 2 is not limited to a circular shape (an annular shape), as with the oscillator array 2 of FIG. 1.

FIG. 15 is a diagram illustrating a shape example of the oscillator array 2 of the ultrasonic imaging apparatus 8 according to the first embodiment.

Figure 15A:
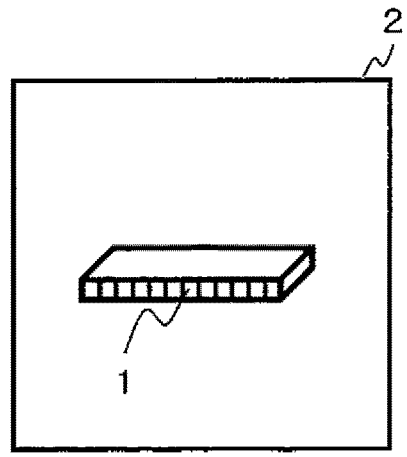
FIG. 15A is a diagram illustrating a shape example of an oscillator array of the ultrasonic imaging apparatus.

In an example of measuring the reflection properties, the oscillator array 2 is configured of the plurality of oscillators 1 which are arranged to measure direction dependency of the ultrasonic signal (the reflection signal) of the reflection wave or to transmit the ultrasonic wave from a plurality of different directions. For example, as illustrated in FIG. 15A, the oscillator array 2 may include the plurality of oscillators 1 arranged on a straight line.

In addition, in an example of measuring the reflection properties, the oscillator array 2 is configured of an one or more oscillators 1, and an oscillator position detection apparatus which detects the position of the oscillator 1, such that the ultrasonic wave is transmitted and received from the multidirection, and the position of the oscillator 1 transmitting and receiving is grasped. In this case, the transmission and reception signal control unit 10 receives position information of the oscillator array 2 from the oscillator position detection apparatus, stores the received position information in the transmission and reception signal control unit 10 and (or) the storage unit 5, and thus, the position information of the oscillator array 2 is used in each of the functional units 10 to 14 of the control computation unit 3.

Figure 15B:
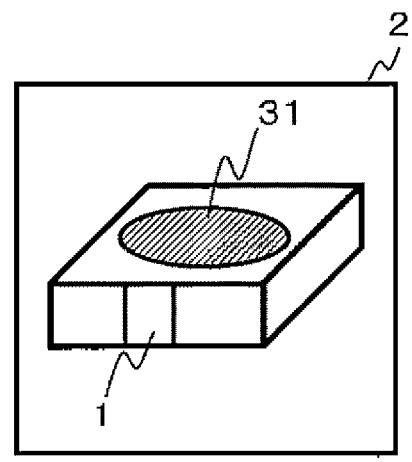
FIG. 15B is a diagram illustrating a shape example of the oscillator array of the ultrasonic imaging apparatus.

For example, as illustrated in FIG. 15B, the oscillator array 2 may be configured of one oscillator 1, and a position sensor 31, which is the oscillator position detection apparatus. In this case, the transmission and reception signal control unit 10 receives the position information of the oscillator 1 from the position sensor 31.

Figure 15C:
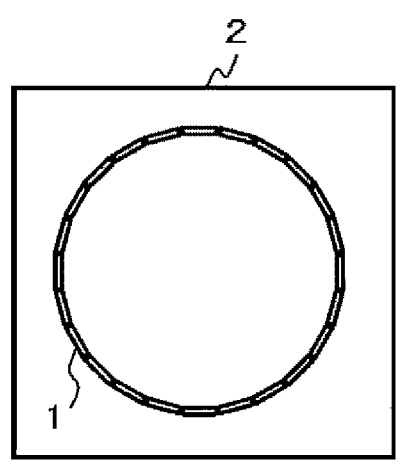
FIG. 15C is a diagram illustrating a shape example of the oscillator array of the ultrasonic imaging apparatus.

In addition, in the case of the measurement of the reflection properties and (or) the measurement of the physical property value, the oscillator array 2 illustrated in FIG. 15C, may be in a shape where the plurality of oscillators 1 surround the subject 7, as with the circular oscillator array 2 of FIG. 1. In the case of the measurement of the reflection properties, in such a configuration, the ultrasonic wave is transmitted and received from any angle with respect to a plane including the oscillator array 2, and thus, the reflection wave is detected at a wide solid angle, compared to a case where the oscillator array 2 does not surround the subject 7. For this reason, in the case of calculating the state information S6 based on the reflection wave, an effect of improving the reliability and (or) the accuracy of the state information S6 can be obtained.

In addition, in the case of the measurement of the physical property value, it is possible to measure a wave transmitted through the subject 7 with respect to all directions in the plane, and thus, it is possible to calculate the acoustic velocity, the attenuation, and the like of the subject 7 by using the ultrasonic tomography method. For this reason, even in the case of calculating the state information S6 based on the transmission wave, the effect of improving the reliability and (or) the accuracy of the state information S6 can be obtained.

In addition, in the oscillator array 2, not all of the oscillators 1 may be mounted on the same substrate, but the oscillators 1 may be mounted on a plurality of substrates.

Figure 15D:
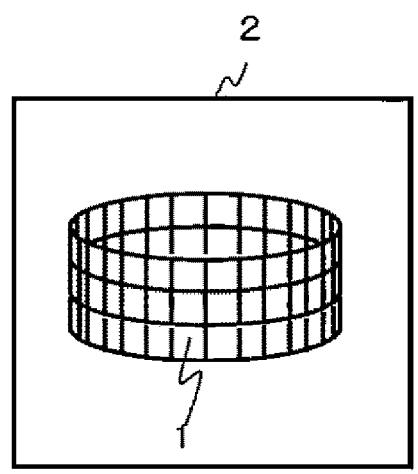
FIG. 15D is a diagram illustrating a shape example of the oscillator array of the ultrasonic imaging apparatus.
Figure 15E:
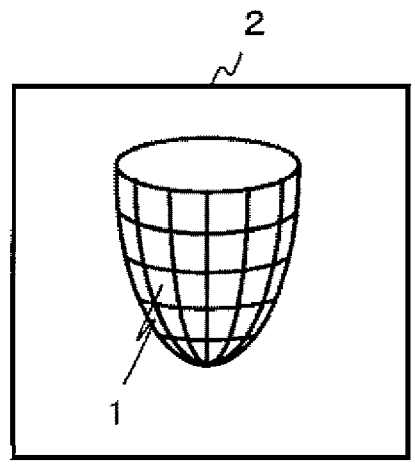
FIG. 15E is a diagram illustrating a shape example of the oscillator array of the ultrasonic imaging apparatus.

In addition, in the case of the measurement of the reflection properties and (or) the measurement of the physical property value, the oscillator array 2 may be configured of the plurality of oscillators 1 which are not arranged on the same plane, but are three-dimensionally arranged. For example, the plurality of oscillators 1 may be arranged on a surface having a shape where the circular array as illustrated in FIG. 15C is stacked in a center axis direction of a circle, as illustrated in FIG. 15D, or a shape where the circular array is stacked in the center axis direction of the circle while gradually increasing the radius of the circular array (for example, the shape of a semi-rugby ball), as illustrated in FIG. 15E.

In the case of the measurement of the reflection properties, the reflection wave is detected at a wide solid angle according to the oscillator array 2 in which the plurality of oscillators 1 are three-dimensionally arranged. For this reason, in a case where the state information S6 based on the reflection wave is calculated, the effect of improving the reliability and (or) the accuracy of the state information S6 can be obtained. In addition, in the case of the measurement of the physical property value, the transmission wave transmitted through the various plane can be measured, and thus, it is possible to calculate the acoustic velocity, the attenuation, and the like of the subject 7 on various planes by using the ultrasonic tomography method, as the state information S6. For this reason, even in the case of calculating the state information S6 based on the transmission wave, the effect of improving the reliability and (or) the accuracy of the state information S6 can be obtained.

Figure 15F:
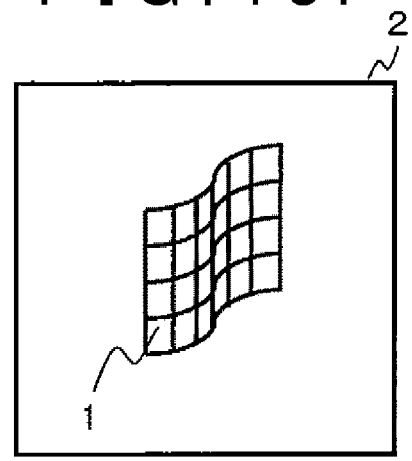
FIG. 15F is a diagram illustrating a shape example of the oscillator array of the ultrasonic imaging apparatus.

In addition, for example, as illustrated in FIG. 15F, in the oscillator array 2, the plurality of oscillators 1 may be attached to a thin flexible sheet-like substrate, and the positional relationships of plurality of oscillators 1 may be changed from each other. In such a configuration, it is possible to obtain the same effect as that in a case where the plurality of oscillators 1 are three-dimensionally arranged.

Further, the positional relationships of the plurality of oscillators 1 are changed from each other, according to the subject 7, and thus, it is possible to obtain the reception signal S2 of the ultrasonic wave regardless of the shape of the subject 7.

In addition, the oscillator array 2 may include an oscillator movement apparatus mechanically moving the oscillator 1, in addition to the oscillator 1. In this case, the transmission and reception signal control unit 10 sets the operation of the oscillator movement apparatus on the basis of the setting of each of the functional units 10 to 14 or the transmission and reception setting information S8, transmits an operation signal with respect to the oscillator movement apparatus on the basis of the setting, and controls the operation of the oscillator movement apparatus.

Figure 15G:
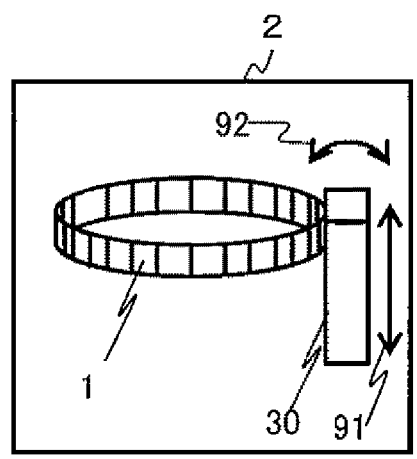
FIG. 15G is a diagram illustrating a shape example of the oscillator array of the ultrasonic imaging apparatus.

For example, as illustrated in FIG. 15G, the oscillator array 2 in which the plurality of oscillators 1 are arranged on the same plane, may be moved by an actuator 30, which is the oscillator movement apparatus, according to the control of the transmission and reception signal control unit 10, and in the oscillator array 2, the ultrasonic wave may be transmitted and received in different positions of the subject 7. A driving direction of the actuator 30 may be a direction 91 in which the oscillator array 2 moves straight-forward, may be a direction 92 in which the angle of the oscillator array 2 is steered around an arbitrary axis, or may be a combination thereof. In addition, the oscillator array 2 is not limited to the circular shape as illustrated in FIG. 15G, but may be in any shape.

In addition, in a case where the oscillator array 2 includes the actuator 30 and a position sensor 31, the transmission and reception signal control unit 10 may performs feedback control such that the operation signal to be transmitted with respect to the actuator 30 is set on the basis of the position information obtained by the position sensor 31, and the oscillator array 2 is moved to a desired position or is retained in a desired position.

Figure 15H:
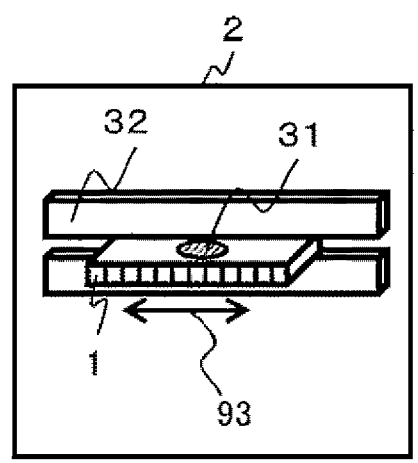
FIG. 15H is a diagram illustrating a shape example of the oscillator array of the ultrasonic imaging apparatus.

In addition, as illustrated in FIG. 15H, the oscillator array 2 may include the plurality of oscillators 1, and the position sensor 31, and the plurality of oscillators 1 may be configured by being attached to a guide 32 restricting a moving direction 93 of the movement of the plurality of oscillators 1. In this case, the position sensor 31 may detect the position information only with respect to the moving direction 93 in which the oscillator array 2 can be moved.

In a case where the oscillator array 2 includes the plurality of oscillators 1, a switch for switching the oscillator 1 transmitting and receiving the ultrasonic wave, may be provided in the oscillator array 2, or the transmission and reception signal control unit 10. Accordingly, it is possible to reduce the number of RF generators generating the transmission signal S1 of the ultrasonic wave, the number of amplifiers, the number of A/D converters, and the like, compared to the number of oscillators 1. In addition, it is possible to reduce an amount of data retained in the storage unit 5.

Second Embodiment

Next, a second embodiment, which is another example of the detailed embodiment of the present invention, will be described. Furthermore, the same reference numerals will be applied to the same portions or the same functions as those of the first embodiment, and repeated description will be omitted.

Figure 16:
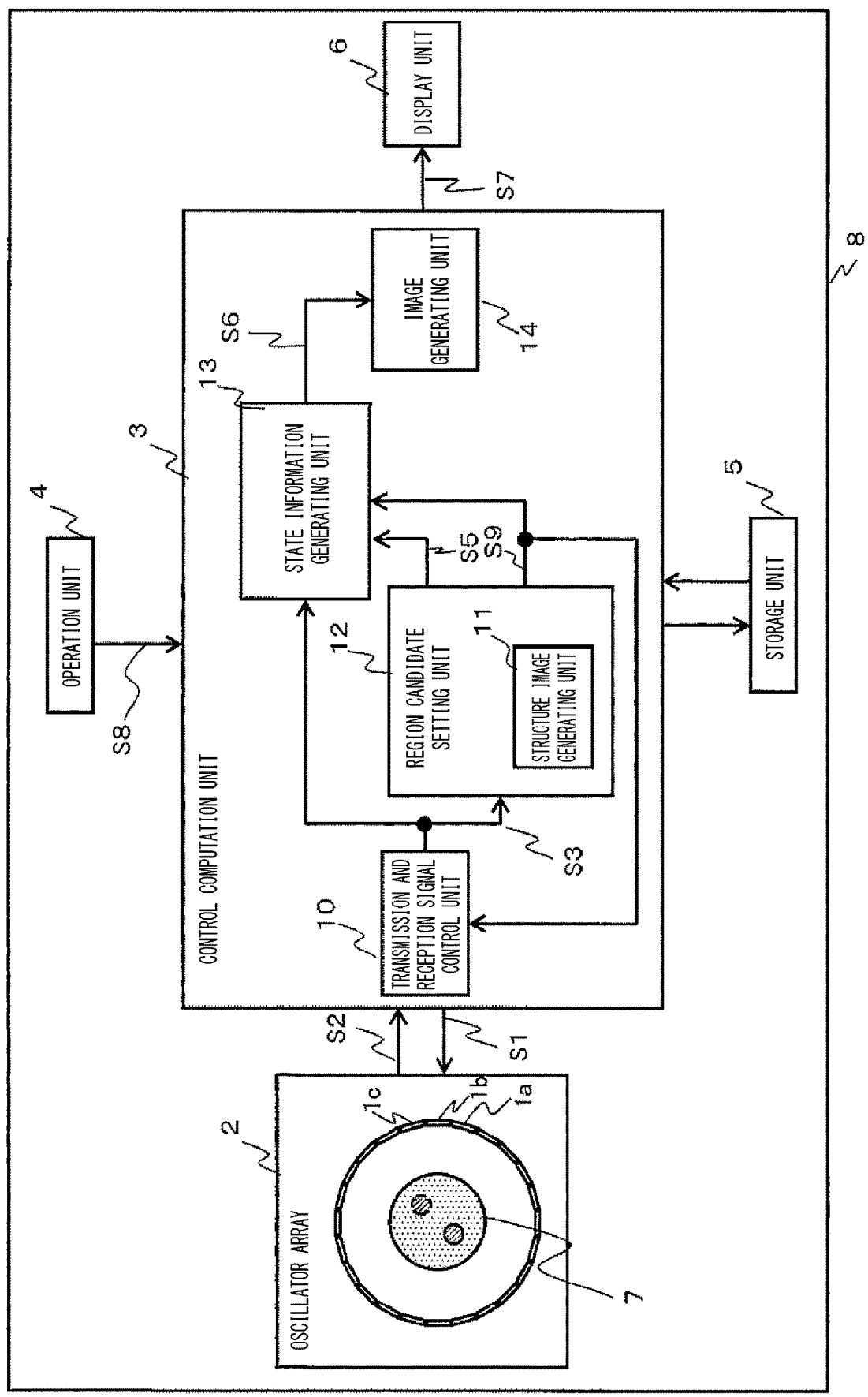
FIG. 16 is an example of a block diagram illustrating a configuration of a control computation unit of a second embodiment.

FIG. 16 is an example of a block diagram illustrating the configuration of the control computation unit 3 of the second embodiment. In the second embodiment, the following functions are added to the ultrasonic imaging apparatus 8 of the first embodiment. That is, as illustrated in FIG. 16, the region candidate setting unit 12 of the control computation unit 3 stores and sets region candidate transmission and reception setting information S9, which is transmission and reception setting including various setting information items at the time of transmitting and receiving the ultrasonic wave with respect to the region candidate S5, in the information storage table group 100 of the storage unit 5, on the basis of the reception signal data S3, in addition to the region candidate S5. In addition, the region candidate setting unit 12 transmits the region candidate transmission and reception setting information S9 to the transmission and reception signal control unit 10 and the state information generating unit 13. Here, the region candidate transmission and reception setting information S9 is transmission and reception setting for transmitting the ultrasonic wave to the region candidate S5 in the subject 7, and for acquiring the reception signal S2 according to at least one of the reflection signal from the reflection point in the region candidate S5 and the transmission signal transmitted through the region candidate S5.

The transmission and reception signal control unit 10 transmits the transmission signal S1 of the ultrasonic wave to the oscillator array 2 on the basis of the region candidate transmission and reception setting information S9, and generates the reception signal data S3 on the basis of the reception signal S2 received from the oscillator array 2, in addition to the transmission and reception setting information S8.

In addition, the state information calculation unit 13 calculates the state information S6 in the region candidate S5, on the basis of the reception signal data S3, the transmission and reception setting information S8, and the region candidate transmission and reception setting information S9.

Figure 17:
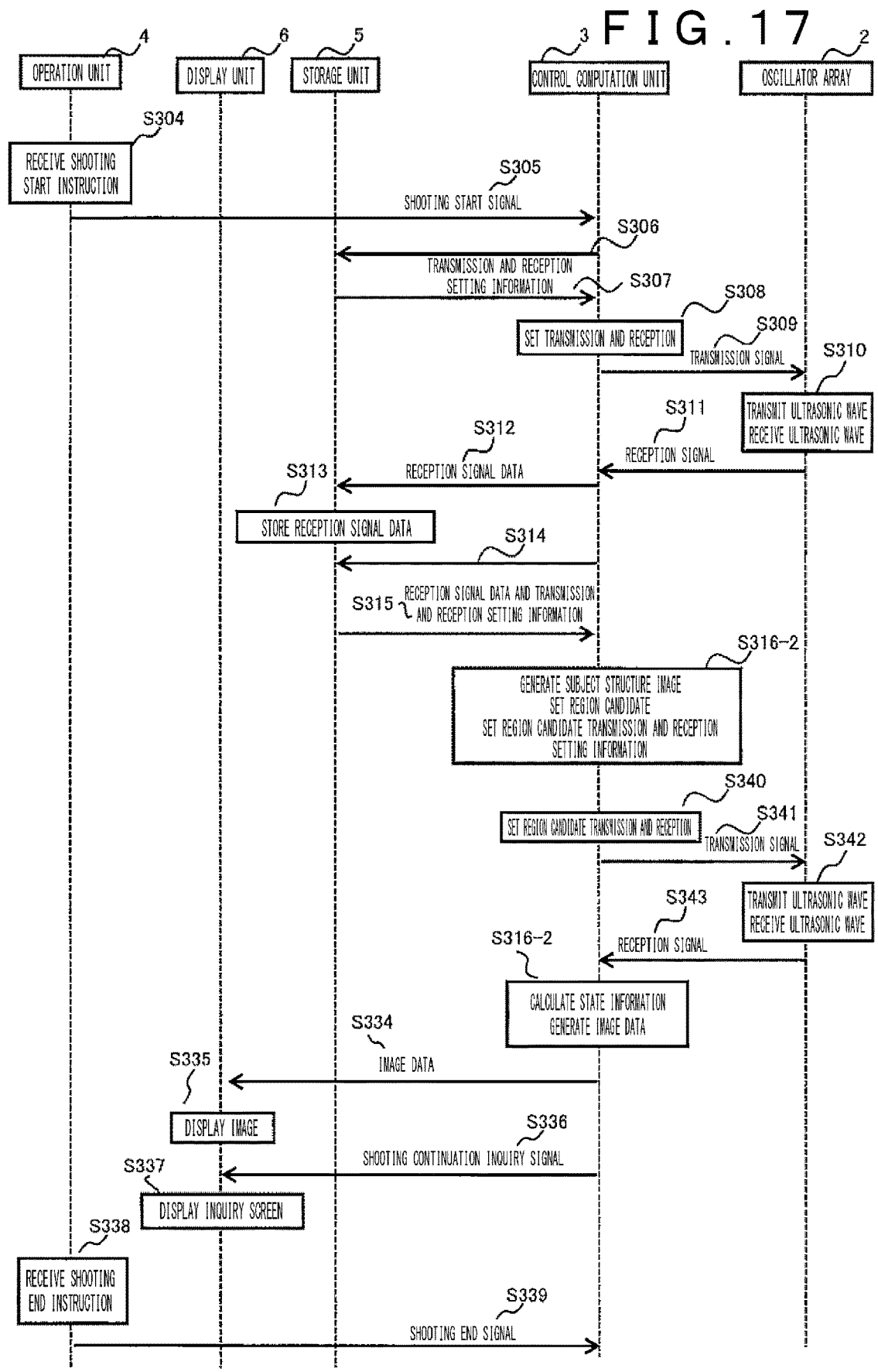
FIG. 17 is an example of a sequence diagram illustrating an operation of an ultrasonic imaging apparatus of the second embodiment.
Figure 18:
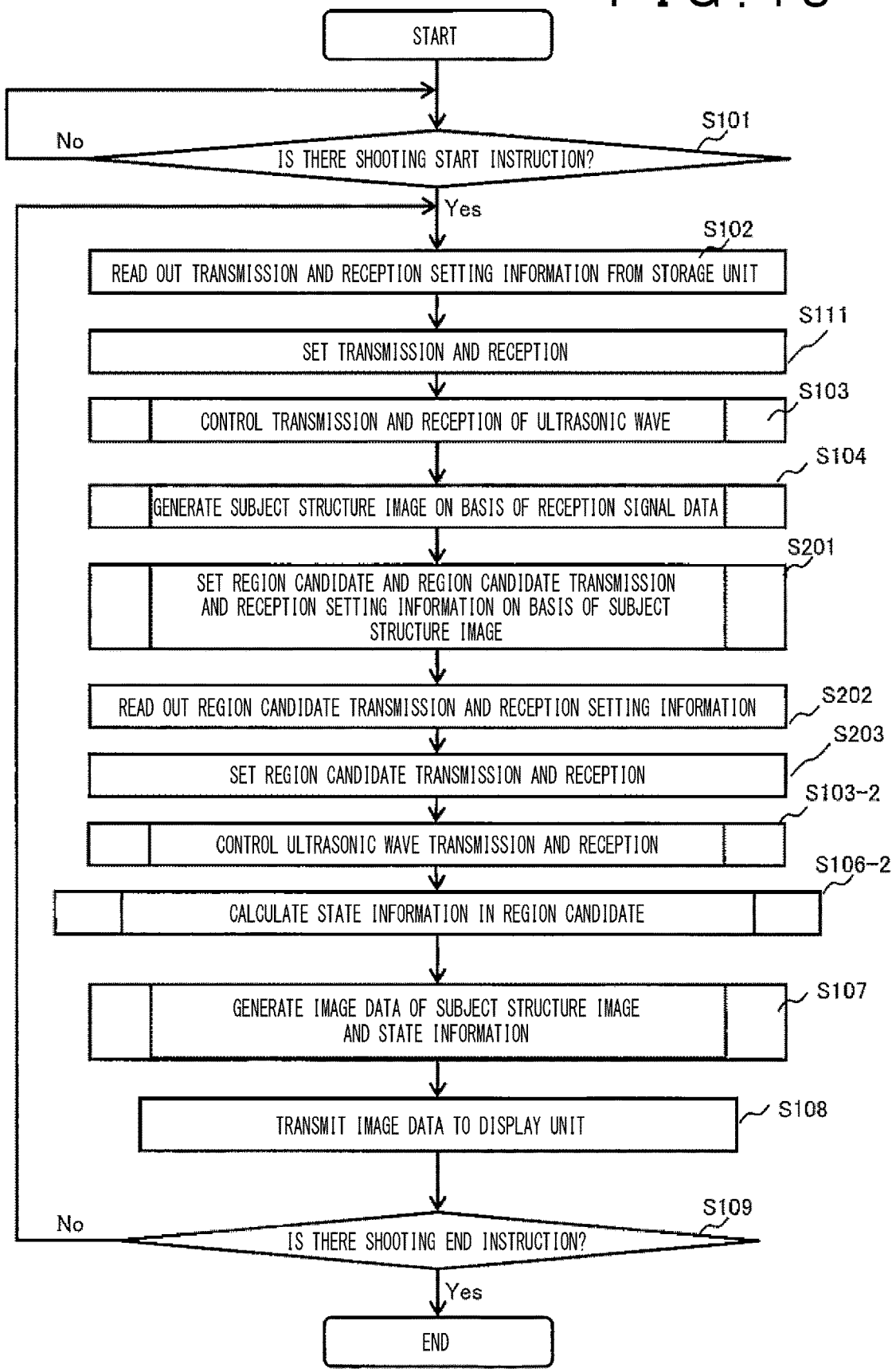
FIG. 18 is an example of a flowchart illustrating the entire flow of the control computation unit of the second embodiment.
Figure 19:
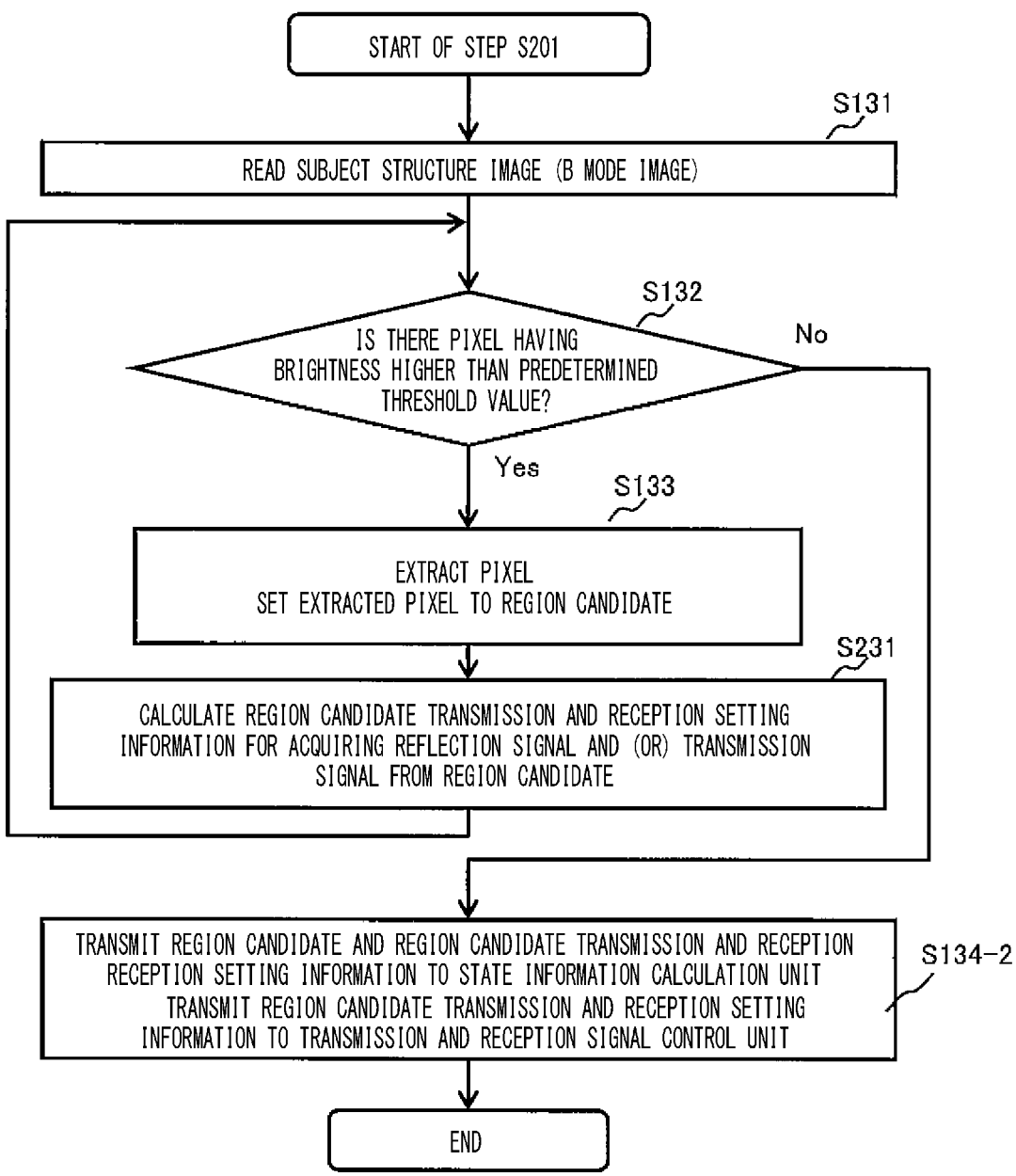
FIG. 19 is an example of a flowchart illustrating an operation of a region candidate setting unit of the second embodiment.

In FIG. 17 to FIG. 19, the operation of the control computation unit 3 will be described in detail. FIG. 17 is an example of a sequence diagram illustrating the operation of the ultrasonic imaging apparatus 8.

As with FIG. 5, first, the ultrasonic imaging apparatus 8 executes Steps S300 to S303 (not illustrated in FIG. 17), and Steps S304 to S315.

Next, the control computation unit 3 receiving the signal data S3 and the transmission and reception setting information S8 for each time of transmission and reception from the storage unit 5 in Step S315, generates the subject structure image S4 on the basis of the reception signal data S3 and the transmission and reception setting information S8, received for each time of transmission and reception, and sets the region candidate S5 and the region candidate transmission and reception setting information S9 on the basis of the subject structure image S4 (S316-2).

Then, the control computation unit 3 transmits the transmission signal S1 to the oscillator array 2, according to the region candidate transmission and reception setting information S9 set in Step S316-2 (S341). The oscillator array receiving the transmission signal S1, transmits the ultrasonic wave into the oscillator array 2, and receives the ultrasonic wave from the oscillator array 2 (S342). The oscillator array 2 converts the received ultrasonic wave into the reception signal S2, and transmits the reception signal S2 to the control computation unit 3 (S343).

The control computation unit 3 calculates the state information S6 on the basis of the reception signal data S3 based on the region candidate transmission and reception setting information S9, and the region candidate S5 and the region candidate transmission and reception setting information S9, set in Step S316-2, and generates the image data S7 on the basis of the subject structure image S4 and the state information S6, generated in Step S316-2 (S316-3). Then, the control computation unit 3 transmits the image data S7 to the display unit 6 (S334).

Next, as with FIG. 5, the ultrasonic imaging apparatus 8 executes Steps S335 to S339, and ends the processing.

FIG. 18 is an example of a flowchart illustrating the entire flow of the operation of the control computation unit 3. As illustrated in FIG. 18, the control computation unit 3, first, executes Steps S101 to S104, as with FIG. 6.

Next, the region candidate setting unit 12 sets the region candidate S5 and the region candidate transmission and reception setting information S9, on the basis of the subject structure image S4 generated in Step S104 (S201). The details of Step S201 will be described below in FIG. 19.

Next, the transmission and reception signal control unit 10 reads out the region candidate transmission and reception setting information S9 stored in the information storage table group 100 from the storage unit 5 (S202), stores the read region candidate transmission and reception setting information S9 in the transmission and reception signal control unit 10, sets the number of times of transmission and reception of the ultrasonic wave (the number of times of transmission and reception), and performs the region candidate transmission and reception setting, which is the transmission and reception setting at the time of transmitting and receiving the ultrasonic wave, with respect to the region candidate S5 such as the setting of the oscillator 1 used for each time of transmission and reception (S203). Then, the transmission and reception signal control unit 10 controls the oscillator array 2 such that the ultrasonic wave is transmitted and received according to the set region candidate transmission and reception setting information S9 (S103-2). As with S103, the operation of the transmission and reception of S103-2, is performed according to each step of FIG. 7.

Next, the state information calculation unit 13 calculates the state information S6 in the region candidate S5 set in Step S201 (S106-2). A procedure of a specific operation is identical to the operation of Step S106 illustrated in FIG. 10, but the transmission and reception setting information S8 read by the state information calculation unit 13 in Step S141 is the region candidate transmission and reception setting information S9, and the reception signal data S3 is the reception signal data S3 stored by allowing the transmission and reception signal control unit 10 to transmit and receive the ultrasonic wave on the basis of the region candidate transmission and reception setting information S9 in Step S103-2.

Next, the control computation unit 3 executes Steps S107 to S109, and repeats a set of measurement, or ends the measurement. In addition, the control computation unit 3 may display a part or all of the image information items S4 to S7 on the display unit 6 during each step of Steps S104, S201, S106-2, and S107 of FIG. 18, in which the image information items S4 to S7 are generated, or between the respective steps, as with the first embodiment, and then, may display a display of inquiring whether or not to continue the processing of the operator, to the operator.

FIG. 19 is an example of a flowchart illustrating the operation of the region candidate setting unit 12. First, the region candidate setting unit 12 reads the subject structure image S4 (the B mode image) (S131). Next, the region candidate setting unit 12 determines whether or not there is a pixel having a brightness higher than a predetermined threshold value, in the pixels in the read subject structure image S4 (S132). In a case where there is a pixel having a brightness higher than the predetermined threshold value (Yes in S132), the region candidate setting unit 12 extracts the pixel, and sets the extracted pixel to the region candidate S5 (S133).

Next, the region candidate setting unit 12 calculates the region candidate transmission and reception setting information S9 for acquiring the reflection signal and (or) the transmission signal from the region candidate S5, on the basis of the region candidate S5 (S231). Specifically, the region candidate setting unit 12 determines the transmission oscillator 50 for each time of transmission, determines delay time applied to each of the oscillators 1 such that the region candidate S5 is set to a transmission focal point, determines other information items, and calculates the region candidate transmission and reception setting information S9. Then, the region candidate setting unit 12 returns to Step S132, and repeatedly executes Steps S132, S133, and S231.

In Step S132, in a case where there is no pixel having a brightness higher than the predetermined threshold value (No in S132), the region candidate setting unit 12 transmits the region candidate S5 and the region candidate transmission and reception setting information S9 to the state information calculation unit 13, transmits the region candidate transmission and reception setting information S9 to the transmission and reception signal control unit 10 (S134-2), and ends the processing. The control computation unit 3 proceeds to Step S202. Furthermore, the region candidate setting unit 12 may transmit the region candidate transmission and reception setting information S9 to the storage unit 5, and may store the region candidate transmission and reception setting information S9 in the storage unit 5.

Furthermore, in Step S132, in a case where there is no region candidate S5 to be transmitted to the state information calculation unit 13, the control computation unit 3 returns to the previous step (any one of Steps S102 to S104, and S111 of FIG. 18), and may perform the measurement again.

As with the first embodiment, the region candidate S5 may be a region surrounded by a closed curve or the like, or may be set for each element unit in the imaging space region. A point that the setting mode of the region candidate S5 is not necessarily limited to the mode of distinguishing the brightness of the subject structure image S4 as described above with the threshold value, is also identical to that of the first embodiment.

In addition, as described above, the region candidate setting unit 12 may calculate the region candidate transmission and reception setting information S9 with respect to each of the pixels of the region candidate S5, or for example, a representative point of the region candidate S5, such as the center of the region candidate S5, may be calculated after the region candidate S5 is completely extracted, and the region candidate transmission and reception setting information S9 for acquiring the reflection signal and (or) the transmission signal from the representative point may be calculated. At this time, there may be one representative point of the region candidate S5, or there may be a plurality of representative points. As described above, the region candidate transmission and reception setting information S9 is limited to the representative point of the region candidate S5, and thus, it is possible to reduce the number of times of transmission and reception, and to reduce measurement time and (or) calculation time.

In addition, as described above, the region candidate setting unit 12 may automatically set the region candidate transmission and reception setting information S9 on the basis of the region candidate S5, and for example, may set the candidate of the region candidate transmission and reception setting information 9, may display the display unit 6, and may allow the operator to input the region candidate transmission and reception setting information S9 set from the candidate of the region candidate transmission and reception setting information 9, into the operation unit 4.

In addition, as with the first embodiment, the region candidate setting unit 12 may set the region candidate S5 on the basis of the reception signal data S3, in Step S133, and may calculate the region candidate transmission and reception setting information 9 from the region candidate S5 based on the reception signal data S3, in Step S231.

As described above, according to this embodiment, the region candidate transmission and reception setting information S9 of the ultrasonic wave is set on the basis of the setting of the region candidate S5, the transmission and reception of the ultrasonic wave is performed according to the setting, and the state information S6 is generated from the acquired reception signal data S3. Therefore, the state information S6 is generated from the reception signal data S3 reflecting the ultrasonic wave from the region candidate S5 according to the region candidate transmission and reception setting information S9, and thus, it is possible to suppress an amount of data, which is necessary for generating the state information S6, and to reduce the measurement time and the amount of data in the ultrasonic imaging apparatus 8, compared to a case where the state information S6 is generated from the reception signal data S3 reflecting the ultrasonic wave from the entire area of the subject 7. In addition, the ultrasonic imaging apparatus 8 of this embodiment generates the state information S6 by using the reception signal data S3 of the region candidate S5 based on the region candidate transmission and reception setting information S9, and thus, it is possible to more accurately generate the state information S6.

As a result thereof, as with the first embodiment, in the application such as the examination, in which it is necessary to display the measurement result for a short period of time, it is possible to utilize the state information S6 of the ultrasonic imaging apparatus 8, to display the measurement result of the subject 7 for a short period of time, and to reduce time for constraining the subject.

Furthermore, the present invention is not limited to the embodiments described above, but includes various modification examples. For example, the embodiments described above have been described in detail in order to easily understand the present invention, but are not limited to have all configurations described above. In addition, a part of a configuration of any embodiment can be substituted with a configuration of the other embodiment, and the configuration of the other embodiment can be added to the configuration of any embodiment. In addition, addition, deletion, or substitution of the other configuration can be performed with respect to a part of the configuration of each of the embodiments. In addition, a part or all of each configuration, each function, each processing unit, each processing section, and the like, described above, for example, may be realized by hardware by being designed as an integrated circuit such as a FPGA. In addition, each configuration, each function, and the like, described above, may be realized by software by allowing a processor to analyze a program for realizing each of the functions. Information of a program, a table, a file, and the like for realizing each of the functions can be stored in a recording apparatus such as a memory, a hard disk, and a solid state drive (SSD), and a recording medium such as an integrated circuit (IC) card, an SD card, and a DVD.

In addition, various information items have been described in the expression of "aaa table", but various information items may be expressed in a data structure other than the table. The "aaa table" can be referred to as "aaa information", in order to represent that it does not depend on the data structure. In addition, it has been described that each information item is recorded in various tables in the expression of "storing", but each information item may be expressed by "registering", "setting", "storing", or "recording".

In addition, a control line or an information line is illustrated in a case where it is considered that the control line or the information line is necessary for the description, but is not limited to necessarily illustrate all control lines or all information lines on the product. In practice, it may be considered that almost all of the configurations are connected to each other.

REFERENCE SIGNS LIST 1 oscillator
2 oscillator array
3 control computation unit
4 operation unit (IF)
5 storage unit
6 display unit
7 subject
8 ultrasonic imaging apparatus
10 transmission and reception signal control unit
11 structure image generating unit
12 region candidate setting unit
13 state information generating unit
14 image generating unit
100 information storage table group
110 transmission setting table
120 reception setting table
S1 transmission signal
S2 reception signal
S3 reception signal data
S4 subject structure image
S5 region candidate
S6 state information
S7 image data
S8 transmission and reception setting information

The invention claimed is:
1. An ultrasonic computed tomography (CT) apparatus, comprising:
an oscillator array which transmits an ultrasonic wave towards a subject, receives the ultrasonic wave, having an interaction with the subject, from a plurality of different angles with respect to the transmitted ultrasonic wave, including receiving a transmission wave, which is an ultrasonic wave transmitted through the subject, or a reflection wave, which is an ultrasonic wave reflected on the subject, and transmits a reception signal based on the transmission wave or the reflection wave;
a processor coupled to the oscillator array and coupled to a memory that stores instructions that when executed by the processor, cause the processor to:
receive the reception signal,
set a tissue region candidate, which is a candidate of a region indicating a tissue of the subject, on the basis of a brightness of each pixel based on the reception signal, divide oscillators of the oscillator array into a plurality of groups, calculate state information, which is information relevant to a state of the tissue in the tissue region candidate, by performing phasing addition based on the reception signal for each pixel of each oscillator group for each time of ultrasonic wave transmission and reception, obtaining an absolute value with respect to the value of the reception signal data subjected to the phasing addition processing for each pixel of the reception oscillator group, and calculating a reception signal intensity for each of the oscillator groups based on a reception signal intensity for each pixel of each oscillator group, generate an ultrasonic image reflecting the state information, on the basis of the state information, and display the ultrasonic image on a display, wherein the processor is further configured to:

generate a subject structure image reflecting a structure of the subject, on the basis of the reception signal, and set at least one of a boundary region candidate, which is a candidate of a region indicating a boundary of the tissue, and an interior region candidate, which is a candidate of a region indicating an interior of the tissue, as the tissue region candidate, on the basis of the calculated state information, wherein in a case where the boundary region candidate is set, the state information is boundary state information, which is information relevant to a state of the boundary in the boundary region candidate and is based on the reception signal, wherein in a case where the interior region candidate is set, the state information is interior state information, which is information relevant to a state of the interior in the interior region candidate and is based on the reception signal, wherein the oscillators of the oscillator array include a plurality of oscillators transmitting and receiving the ultrasonic wave, and wherein the processor is further configured to:

change a reception oscillator, which is an oscillator receiving the ultrasonic wave, whenever the ultrasonic wave is received, and calculate the state information on the basis of the reception signal of which the reception oscillator has changed, and the tissue region candidate.

2. The ultrasonic CT apparatus according to claim 1, wherein the processor is further configured to:

calculate a physical property value of the subject from the reception signal based on the transmission wave by an ultrasonic tomography method, and generate the subject structure image by using the calculated physical property value, in a case where the reception signal is based on the transmission wave.

3. The ultrasonic CT apparatus according to claim 1, wherein the processor is further configured to:

calculate the boundary state information on the basis of the reception signal based on the reflection wave, and the boundary region candidate, or calculate the interior state information on the basis of the reception signal based on the reflection wave, and the interior region candidate, in a case where the reception signal is based on the reflection wave, and calculate the boundary state information on the basis of the reception signal based on the transmission wave and the boundary region candidate, or calculate the interior state information on the basis of the reception signal based on the transmission wave and the interior region candidate, in a case where the reception signal is based on the transmission wave.

4. The ultrasonic CT apparatus according to claim 1, wherein the processor is further configured to:

change a transmission oscillator, which is an oscillator transmitting the ultrasonic wave, whenever the ultrasonic wave is transmitted, and calculate the state information on the basis of the reception signal of which the transmission oscillator has changed, and the tissue region candidate.

5. The ultrasonic CT apparatus according to claim 1, wherein the processor is further configured to calculate each reception signal intensity distribution corresponding to the tissue region candidate in the reception signals, calculate a correlation or a degree of similarity between the relative intensity distributions or amounts of statistics based on each of the intensity distributions, and set the calculated correlation or degree of similarity to the state information.

6. The ultrasonic CT apparatus according to claim 4, wherein the processor is further configured to calculate each reception signal intensity distribution corresponding to the tissue region candidate in the reception signals of a current transmission oscillator, calculate a correlation or a degree of similarity between the respective intensity distributions or amounts of statistics based on each of the intensity distributions, and set the calculated correlation or degree of similarity to the state information.

7. The ultrasonic CT apparatus according to claim 1, wherein the processor is further configured to calculate each reception signal intensity distribution corresponding to the tissue region candidate in the reception signals of which a current reception oscillator, calculate a correlation or a degree of similarity between the relative intensity distributions or amounts of statistics based on each of the intensity distributions, and set the calculated correlation or degree of similarity to the state information.

8. The ultrasonic CT apparatus according to claim 1, wherein the processor is further configured to display the subject structure image along with the ultrasonic image on the display.

9. The ultrasonic CT apparatus according to claim 8, wherein the processor is further configured to display the ultrasonic image to be superimposed on the tissue region candidate in the subject structure image on the display.

10. The ultrasonic CT apparatus according to claim 1, wherein in the oscillator array, the plurality of oscillators transmitting and receiving the ultrasonic wave are two-dimensionally or three-dimensionally arranged, and wherein the plurality of oscillators are arranged to surround the subject.

11. The ultrasonic CT apparatus according to claim 1, wherein the oscillator array transmits the ultrasonic wave towards the tissue region candidate, and transmits the reception signal based on the ultrasonic wave received from the tissue region candidate to the signal receiving unit, and wherein the processor is further configured to calculate the state information, on the basis of the reception signal based on the ultrasonic wave received from the tissue region candidate, and the tissue region candidate.

12. An ultrasonic imaging method of an ultrasonic computed tomography (CT) apparatus, the method comprising:
- a step of transmitting an ultrasonic wave, by an oscillator array, towards a subject, and of receiving the ultrasonic wave, having an interaction with the subject, from a plurality of different angles with respect to the transmitted ultrasonic wave, including receiving a transmission wave, by the oscillator array, transmitted through the subject or a reflection wave reflected on the subject;
- a step of generating a reception signal on the basis of the transmission wave or the reflection wave;
- a step of setting a tissue region candidate, which is a candidate of a region indicating a tissue of the subject, on the basis of a brightness of each pixel based on the reception signal;
- a step of dividing oscillators of the oscillator array into a plurality of groups,
- a step of calculating state information, which is information relevant to a state of the tissue in the tissue region candidate, by
  - performing phasing addition based on the reception signal for each pixel of each oscillator group for each time of ultrasonic wave transmission and reception, obtaining an absolute value with respect to the value of the reception signal data subjected to the phasing addition processing for each pixel of the reception oscillator group, and calculating a reception signal intensity for each of the oscillator groups based on a reception signal intensity for each pixel of each oscillator group;
- a step of generating an ultrasonic image reflecting the state information, on the basis of the state information; and
- a step of displaying the ultrasonic image wherein the method further comprises:
- a step of generating a subject structure image reflecting a structure of the subject, on the basis of the reception signal, and set at least one of a boundary region candidate, which is a candidate of a region indicating a boundary of the tissue, and an interior region candidate, which is a candidate of a region indicating an interior of the tissue, as the tissue region candidate, on the basis of the calculated state information, wherein in a case where the boundary region candidate is set, the state information is boundary state information, which is information relevant to a state of the boundary in the boundary region candidate and is based on the reception signal, wherein in a case where the interior region candidate is set, the state information is interior state information, which is information relevant to a state of the interior in the interior region candidate and is based on the reception signal, wherein the oscillators of the oscillator array include a plurality of oscillators transmitting and receiving the ultrasonic wave, and wherein the method further comprises:
- a step of changing a reception oscillator, which is an oscillator receiving the ultrasonic wave, whenever the ultrasonic wave is received, and
- a step of calculating the state information on the basis of the reception signal of which the reception oscillator has changed, and the tissue region candidate.

* * * * *